(12) United States Patent
Xu et al.

(10) Patent No.: US 11,571,400 B2
(45) Date of Patent: *Feb. 7, 2023

(54) ACAT1 INHIBITORS FOR TREATING CANCER

(71) Applicant: Shanghai Institutes for Biological Sciences, Chinese Academy of Sciences, Shanghai (CN)

(72) Inventors: Chenqi Xu, Shanghai (CN); Boliang Li, Shanghai (CN); Wei Yang, Shanghai (CN); Yibing Bai, Shanghai (CN); Ying Xiong, Shanghai (CN)

(73) Assignee: Center for Excellence in Molecular Cell Science, Chinese Academy of Sciences, Shanghai (CN)

( * ) Notice: Subject to any disclaimer, the term of this patent is extended or adjusted under 35 U.S.C. 154(b) by 540 days.

This patent is subject to a terminal disclaimer.

(21) Appl. No.: 16/069,135

(22) PCT Filed: Jan. 11, 2017

(86) PCT No.: PCT/CN2017/070813
§ 371 (c)(1),
(2) Date: Jul. 10, 2018

(87) PCT Pub. No.: WO2017/121318
PCT Pub. Date: Jul. 20, 2017

(65) Prior Publication Data
US 2019/0060255 A1 Feb. 28, 2019

(30) Foreign Application Priority Data

Jan. 11, 2016 (CN) .......................... 201610015212.6
Jan. 11, 2016 (CN) .......................... 201610015530.2

(51) Int. Cl.
| | |
|---|---|
| *A61K 31/145* | (2006.01) |
| *A61K 31/655* | (2006.01) |
| *A61P 35/00* | (2006.01) |
| *A61K 39/395* | (2006.01) |
| *A61K 31/255* | (2006.01) |
| *A61K 45/00* | (2006.01) |
| *A61K 45/06* | (2006.01) |
| *A61K 31/496* | (2006.01) |
| *A61K 31/4188* | (2006.01) |
| *A61K 31/495* | (2006.01) |
| *C07K 16/28* | (2006.01) |
| *A61K 39/00* | (2006.01) |

(52) U.S. Cl.
CPC .......... *A61K 31/145* (2013.01); *A61K 31/255* (2013.01); *A61K 31/4188* (2013.01); *A61K 31/495* (2013.01); *A61K 31/496* (2013.01); *A61K 31/655* (2013.01); *A61K 39/395* (2013.01); *A61K 39/3955* (2013.01); *A61K 45/00* (2013.01); *A61K 45/06* (2013.01); *A61P* *35/00* (2018.01); *C07K 16/2818* (2013.01); *A61K 2039/505* (2013.01); *C07K 2317/76* (2013.01)

(58) Field of Classification Search
CPC ................ A61K 31/145; A61K 31/655; A61K 39/3955; A61K 2039/505; A61P 35/00; C07K 16/2818
USPC ........................................................ 424/172.1
See application file for complete search history.

(56) References Cited

U.S. PATENT DOCUMENTS

2016/0199497 A1* 7/2016 Cheng .................. A61K 49/008
514/517

FOREIGN PATENT DOCUMENTS

| | | |
|---|---|---|
| CN | 103536922 A | 1/2014 |
| WO | 2013/016315 A1 | 1/2013 |
| WO | 2013/019932 A1 | 2/2013 |
| WO | 2015/065595 A1 | 5/2015 |

OTHER PUBLICATIONS

Gura (Science. 1997; 278: 1041-1042).*
Dennis (Nature. Aug. 7, 2006; 442: 739-741).*
Makino et al. (Neurol Med Chir (Tokyo), 2007, 47: 229-232).*
Yang, W. et al., Potentiating the antitumour response of CD8+ T cells by modulating cholesterol metabolism, NATURE, 2016, vol. 531, No. 7596, pp. 651-655.
Bemlih, S. et al., Acyl-coenzyme A: Cholesterol acyltransferase inhibitor Avasimibe affect survival and proliferation of glioma tumor cell lines, Cancer Biology & Therapy, 2010, vol. 9, No. 12, pp. 1025-1032.
Huttunen, H.J. et al., Knockdown of ACAT-1 reduces amyloidogenic processing of APP, FEBS Letters, 2007, vol. 581, No. 8, pp. 1688-1692.
Apetoh et al. Combining immunotherapy and anticancer agents: the right path to achieve cancer cure? Annals of Oncology 26: 1813-1823, 2015 doi:10.1093/annonc/mdv209.
Dai et al. "Water soluble multiarm-polyethylene glycol-betulinic acid prodrugs: design, synthesis, and in vivo effectiveness". Polym. Chem., 2014, 5, 5775.

(Continued)

*Primary Examiner* — Yan Xiao
(74) *Attorney, Agent, or Firm* — Banner & Witcoff, Ltd.

(57) ABSTRACT

The present disclosure relates to methods and compositions for the treatment of cancer using an ACAT1 inhibitor. The cancer may be any of melanoma, lymphoma, esophageal cancer, liver cancer, head and neck cancer, bladder cancer, endometrial cancer, kidney cancer and thyroid cancer. In some embodiments, the cancer itself it not responsive directly to the ACAT1 inhibitor but is rather treated through the immune system activated by the ACAT1 inhibitor. Combination therapies are also provided, for instance in combination with an alkylating antineoplastic agent.

15 Claims, 13 Drawing Sheets
Specification includes a Sequence Listing.

(56) References Cited

OTHER PUBLICATIONS

Liu et al. "Apoptotic activity of betulinic acid derivatives on murine melanoma B16 cell line". European Journal of Pharmacology 498 (2004) 71-78.

* cited by examiner

SEQUENCE LISTING

<160> NUMBER OF SEQ ID NOS: 30

<210> SEQ ID NO 1
<211> LENGTH: 22
<212> TYPE: DNA
<213> ORGANISM: Artificial
<220> FEATURE:
<223> OTHER INFORMATION: Acat1 Forward primer

<400> SEQUENCE: 1
gaaaccggct gtcaaaatct gg                                    22

<210> SEQ ID NO 2
<211> LENGTH: 23
<212> TYPE: DNA
<213> ORGANISM: Artificial
<220> FEATURE:
<223> OTHER INFORMATION: Acat1 Reverse primer

<400> SEQUENCE: 2
tgtgaccatt tctgtatgtg tcc                                   23

<210> SEQ ID NO 3
<211> LENGTH: 21
<212> TYPE: DNA
<213> ORGANISM: Artificial
<220> FEATURE:
<223> OTHER INFORMATION: Acat2 Forward primer

<400> SEQUENCE: 3
acaagacaga cctcttccct c                                     21

<210> SEQ ID NO 4
<211> LENGTH: 20
<212> TYPE: DNA
<213> ORGANISM: Artificial
<220> FEATURE:
<223> OTHER INFORMATION: Acat2 Reverse primer

<400> SEQUENCE: 4
atggttcgga aatgttcacc                                       20

<210> SEQ ID NO 5
<211> LENGTH: 22
<212> TYPE: DNA
<213> ORGANISM: Artificial
<220> FEATURE:
<223> OTHER INFORMATION: Nceh Forward primer

<400> SEQUENCE: 5
ttgaatacag gctagtccca ca                                    22

<210> SEQ ID NO 6
<211> LENGTH: 23
<212> TYPE: DNA
<213> ORGANISM: Artificial
<220> FEATURE:
<223> OTHER INFORMATION: Nceh Reverse primer

<400> SEQUENCE: 6
caacgtaggt aaactgttgt ccc                                   23

<210> SEQ ID NO 7
<211> LENGTH: 19
<212> TYPE: DNA
<213> ORGANISM: Artificial
<220> FEATURE:
<223> OTHER INFORMATION: Srebp1 Forward primer

<400> SEQUENCE: 7
gcagccacca tctagcctg                                        19

<210> SEQ ID NO 8
<211> LENGTH: 21

-continued

<212> TYPE: DNA
<213> ORGANISM: Artificial
<220> FEATURE:
<223> OTHER INFORMATION: Srebp1 Reverse primer

<400> SEQUENCE: 8
cagcagtgag tctgccttga t                                             21

<210> SEQ ID NO 9
<211> LENGTH: 19
<212> TYPE: DNA
<213> ORGANISM: Artificial
<220> FEATURE:
<223> OTHER INFORMATION: Srebp2 Forward primer

<400> SEQUENCE: 9
gcagcaacgg gaccattct                                                19

<210> SEQ ID NO 10
<211> LENGTH: 23
<212> TYPE: DNA
<213> ORGANISM: Artificial
<220> FEATURE:
<223> OTHER INFORMATION: Srebp2 Reverse primer

<400> SEQUENCE: 10
ccccatgact aagtccttca act                                           23

<210> SEQ ID NO 11
<211> LENGTH: 21
<212> TYPE: DNA
<213> ORGANISM: Artificial
<220> FEATURE:
<223> OTHER INFORMATION: Acaca Forward primer

<400> SEQUENCE: 11
atgggcggaa tggtctcttt c                                             21

<210> SEQ ID NO 12
<211> LENGTH: 21
<212> TYPE: DNA
<213> ORGANISM: Artificial
<220> FEATURE:
<223> OTHER INFORMATION: Acaca Reverse primer

<400> SEQUENCE: 12
tggggacctt gtcttcatca t                                             21

<210> SEQ ID NO 13
<211> LENGTH: 21
<212> TYPE: DNA
<213> ORGANISM: Artificial
<220> FEATURE:
<223> OTHER INFORMATION: Fasn Forward primer

<400> SEQUENCE: 13
ggaggtggtg atagccggta t                                             21

<210> SEQ ID NO 14
<211> LENGTH: 21
<212> TYPE: DNA
<213> ORGANISM: Artificial
<220> FEATURE:
<223> OTHER INFORMATION: Fasn Reverse primer

<400> SEQUENCE: 14
tgggtaatcc atagagccca g                                    21

<210> SEQ ID NO 15
<211> LENGTH: 22
<212> TYPE: DNA
<213> ORGANISM: Artificial
<220> FEATURE:
<223> OTHER INFORMATION: Hmgcs Forward primer

<400> SEQUENCE: 15
aactggtgca gaaatctcta gc                                   22

<210> SEQ ID NO 16
<211> LENGTH: 23
<212> TYPE: DNA
<213> ORGANISM: Artificial
<220> FEATURE:
<223> OTHER INFORMATION: Hmgcs Reverse primer

<400> SEQUENCE: 16
ggttgaatag ctcagaacta gcc                                  23

<210> SEQ ID NO 17
<211> LENGTH: 21
<212> TYPE: DNA
<213> ORGANISM: Artificial
<220> FEATURE:
<223> OTHER INFORMATION: Hmgcr Forward primer

<400> SEQUENCE: 17
agcttgcccg aattgtatgt g                                    21

<210> SEQ ID NO 18
<211> LENGTH: 23
<212> TYPE: DNA
<213> ORGANISM: Artificial
<220> FEATURE:
<223> OTHER INFORMATION: Hmgcr Reverse primer

<400> SEQUENCE: 18
tctgttgtga accatgtgac ttc                                  23

<210> SEQ ID NO 19
<211> LENGTH: 22
<212> TYPE: DNA
<213> ORGANISM: Artificial
<220> FEATURE:
<223> OTHER INFORMATION: Sqle Forward primer

<400> SEQUENCE: 19
ataagaaatg cggggatgtc ac                                   22

<210> SEQ ID NO 20
<211> LENGTH: 21
<212> TYPE: DNA
<213> ORGANISM: Artificial
<220> FEATURE:
<223> OTHER INFORMATION: Sqle Reverse primer

<400> SEQUENCE: 20
atatccgaga aggcagcgaa c                                    21

<210> SEQ ID NO 21
<211> LENGTH: 21
<212> TYPE: DNA
<213> ORGANISM: Artificial

```
<220> FEATURE:
<223> OTHER INFORMATION: Ldlr Forward primer

<400> SEQUENCE: 21
tgactcagac gaacaaggct g                                              21

<210> SEQ ID NO 22
<211> LENGTH: 21
<212> TYPE: DNA
<213> ORGANISM: Artificial
<220> FEATURE:
<223> OTHER INFORMATION: Ldlr Reverse primer

<400> SEQUENCE: 22
atctaggcaa tctcggtctc c                                              21

<210> SEQ ID NO 23
<211> LENGTH: 20
<212> TYPE: DNA
<213> ORGANISM: Artificial
<220> FEATURE:
<223> OTHER INFORMATION: Idol Forward primer

<400> SEQUENCE: 23
tgcaggcgtc tagggatcat                                                20

<210> SEQ ID NO 24
<211> LENGTH: 21
<212> TYPE: DNA
<213> ORGANISM: Artificial
<220> FEATURE:
<223> OTHER INFORMATION: Idol Reverse primer

<400> SEQUENCE: 24
gtttaaggcg gtaaggtgcc a                                              21

<210> SEQ ID NO 25
<211> LENGTH: 21
<212> TYPE: DNA
<213> ORGANISM: Artificial
<220> FEATURE:
<223> OTHER INFORMATION: Abca1 Forward primer

<400> SEQUENCE: 25
aaaaccgcag acatccttca g                                              21

<210> SEQ ID NO 26
<211> LENGTH: 21
<212> TYPE: DNA
<213> ORGANISM: Artificial
<220> FEATURE:
<223> OTHER INFORMATION: Abca1 Reverse primer

<400> SEQUENCE: 26
cataccgaaa ctcgttcacc c                                              21

<210> SEQ ID NO 27
<211> LENGTH: 22
<212> TYPE: DNA
<213> ORGANISM: Artificial
<220> FEATURE:
<223> OTHER INFORMATION: Abcg1 Forward primer

<400> SEQUENCE: 27
ctttcctact ctgtacccga gg                                             22
```

```
<210> SEQ ID NO 28
<211> LENGTH: 21
<212> TYPE: DNA
<213> ORGANISM: Artificial
<220> FEATURE:
<223> OTHER INFORMATION: Abcg1 Reverse primer

<400> SEQUENCE: 28
cggggcattc cattgataag g                                              21

<210> SEQ ID NO 29
<211> LENGTH: 21
<212> TYPE: DNA
<213> ORGANISM: Artificial
<220> FEATURE:
<223> OTHER INFORMATION: Ifng Forward primer

<400> SEQUENCE: 29
atgaacgcta cacactgcat c                                              21

<210> SEQ ID NO 30
<211> LENGTH: 21
<212> TYPE: DNA
<213> ORGANISM: Artificial
<220> FEATURE:
<223> OTHER INFORMATION: Ifng Reverse primer

<400> SEQUENCE: 30
ccatcctttt gccagttcct c                                              21
```

ACAT1 INHIBITORS FOR TREATING CANCER

CROSS-REFERENCE TO RELATED APPLICATIONS

This application is a National Stage Application under 35 U.S.C. 371 of co-pending PCT application PCT/CN2017/070813 designating the United States and filed Jan. 11, 2017; which claims the benefit of Chinese Patent Application No.: 201610015212.6, and filed Jan. 11, 2016; and Chinese Patent Application No.: 201610015530.2, filed Jan. 11, 2016 each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 12, 2021, is named Sequence_Listing_008703_00011ST25.txt and is 5,791 bytes in size.

BACKGROUND

CD8+ T cells play a central role in antitumor immunity, but their activity is suppressed in the tumor microenvironment. Reactivating the cytotoxicity of CD8+ T cells is of great clinical interest in cancer immunotherapy. However, tumor can escape immune attack by various mechanisms of immunosuppression. It is therefore of great clinical interest to develop other therapies to potentiate the antitumor activity of $CD8^+$ T cells by modulating different pathways.

SUMMARY

It is discovered herein that the antitumor response of CD8+ T cells can be potentiated by modulating cholesterol metabolism. Inhibiting cholesterol esterification in T cells by genetic ablation or pharmacological inhibition of ACAT1 (acyl-coenzyme A:cholesterol acyltransferases 1), a key cholesterol esterification enzyme, led to potentiated effector function and enhanced proliferation of CD8+ T cells. This is attributed to the elevation of the plasma membrane cholesterol level of CD8+ T cells that causes enhanced T-cell receptor clustering and signaling as well as more efficient formation of immunological synapse.

In accordance with one embodiment of the present disclosure, provided is a method for treating a cancer in a patient in need thereof. The method may entail administering to the patient a therapeutically effective amount of an acyl-coenzyme A:cholesterol acyltransferases 1 (ACAT1) inhibitor.

Non-limiting examples of cancers suitable for the treatment include melanoma, lymphoma, esophageal cancer, liver cancer, head and neck cancer, bladder cancer, endometrial cancer, kidney cancer, thyroid cancer, breast cancer, colorectal cancer, leukemia, lung cancer, pancreatic cancer, and prostate cancer. In some embodiments, the cancer is selected from the group consisting of melanoma, lymphoma, esophageal cancer, liver cancer, head and neck cancer, bladder cancer, endometrial cancer, kidney cancer and thyroid cancer.

In one embodiment, the cancer is melanoma, such as Lentigo maligna, Lentigo maligna melanoma, superficial spreading melanoma, acral lentiginous melanoma, mucosal melanoma, nodular melanoma, polyploid melanoma, desmoplastic melanoma, amelanotic melanoma, and soft-tissue melanoma.

Cancer patients with a suppressed CD8+ T cell in a tumor microenvironment are suitable for the presently disclosed treatment. In some embodiments, the suppressed CD8+ T cell has reduced cytotoxic activity, reduced proliferative activity or reduced infiltration activity as compared to a CD8+ T cell not in the tumor microenvironment.

In some of the cancer patients, the cancerous or tumor cells themselves may not be responsive directly to the ACAT1 inhibitor. Or, the ACAT1 inhibitor is not cytotoxic to the cancer. Rather, the ACAT1 can activate a CD8+ T cell which exhibits antitumor activity.

In some embodiments, the ACAT1 inhibitor can be selected from a group consisting of a small inhibitory RNA (siRNA), a small hairpin RNA (shRNA), a microRNA (miRNA), or an anti-sense nucleic acid, (B) an ACAT1 inhibitory antibody or fragment thereof, (C) a small molecule inhibitor, and combinations thereof. In some embodiments, the ACAT1 inhibitor is selected from a group consisting of avasimibe (CI-1011), pactimibe, purpactins, manassantin A, diphenylpyridazine derivatives, glisoprenin A, CP113,818, K604, beauveriolide I, beauveriolide III, U18666A, TMP-153, YM750, GERI-BP002-A, Sandoz Sah 58-035, VULM 1457, Lovastatin, CI976, CL-283,546, CI-999, E5324, YM17E, FR182980, ATR-101 (PD132301 or PD132301-2), F-1394, HL-004, F-12511 (eflucimibe), cinnamic acid derivatives, cinnamic derivative, Dup 128, RP-73163, pyripyropene C, FO-1289, AS-183, SPC-15549, FO-6979, Angekica, ginseng, Decursin, terpendole C, beauvericin, spylidone, pentacecilides, CL-283,546, betulinic acid, shikonin derivatives, esculeogenin A, Wu-V-23, pyripyropene derivatives A, B, and D, glisoprenin B-D, saucerneol B, sespendole, diethyl pyrocarbonate, beauveriolide analogues, Acaterin, DL-melinamide, PD 138142-15, CL277,082, EAB-309, Enniatin antibiotics, Epi-cochlioquinone A, FCE-27677, FR186485, FR190809, NTE-122, obovatol, panaxadiols, protopanaxadiols, polyacetylenes, SaH 57-118, AS-186, BW-447A, 447C88, T-2591, TEI-6522, TEI-6620, XP 767, XR 920, GERI-BP001, gomisin N, gypsetin, helminthosporol, TS-962, isochromophilones, kudingosides, lateritin, naringenin, and combinations thereof. In one embodiment, the ACAT1 inhibitor is avasimibe, K604, or CP113,818. In one embodiment, the ACAT1 inhibitor is avasimibe.

The ACAT1 inhibitor can be administered intravenously, intramuscularly, parenterally, nasally, or orally, in some embodiments.

The ACAT1 inhibitor can be conjugated to a targeting molecule that recognizes the CD8+ T cell. The targeting molecule may be an antibody or fragment thereof.

Also disclosed, in some embodiments, is a method for treating a cancer in a patient, comprising administering to the patient a therapeutically effective amount of an acyl-coenzyme A:cholesterol acyltransferases 1 (ACAT1) inhibitor and a second anticancer agent. An example anticancer agent is an alkylating antineoplastic agent, which can be a triazene. Non-limiting examples of triazene include dacarbazine, mitozolomide and temozolomide. In one embodiment, the triazene is dacarbazine. In one embodiment, the ACAT1 inhibitor is avasimibe. The ACAT1 inhibitor can be administered prior to, after, or concurrently with the alkylating antineoplastic agent, without limitation.

Compositions are also provided. In one embodiment, the composition comprises an acyl-coenzyme A:cholesterol acyltransferases 1 (ACAT1) inhibitor and a second anticancer agent such as an alkylating antineoplastic agent.

DETAILED DESCRIPTION

Figure 1:
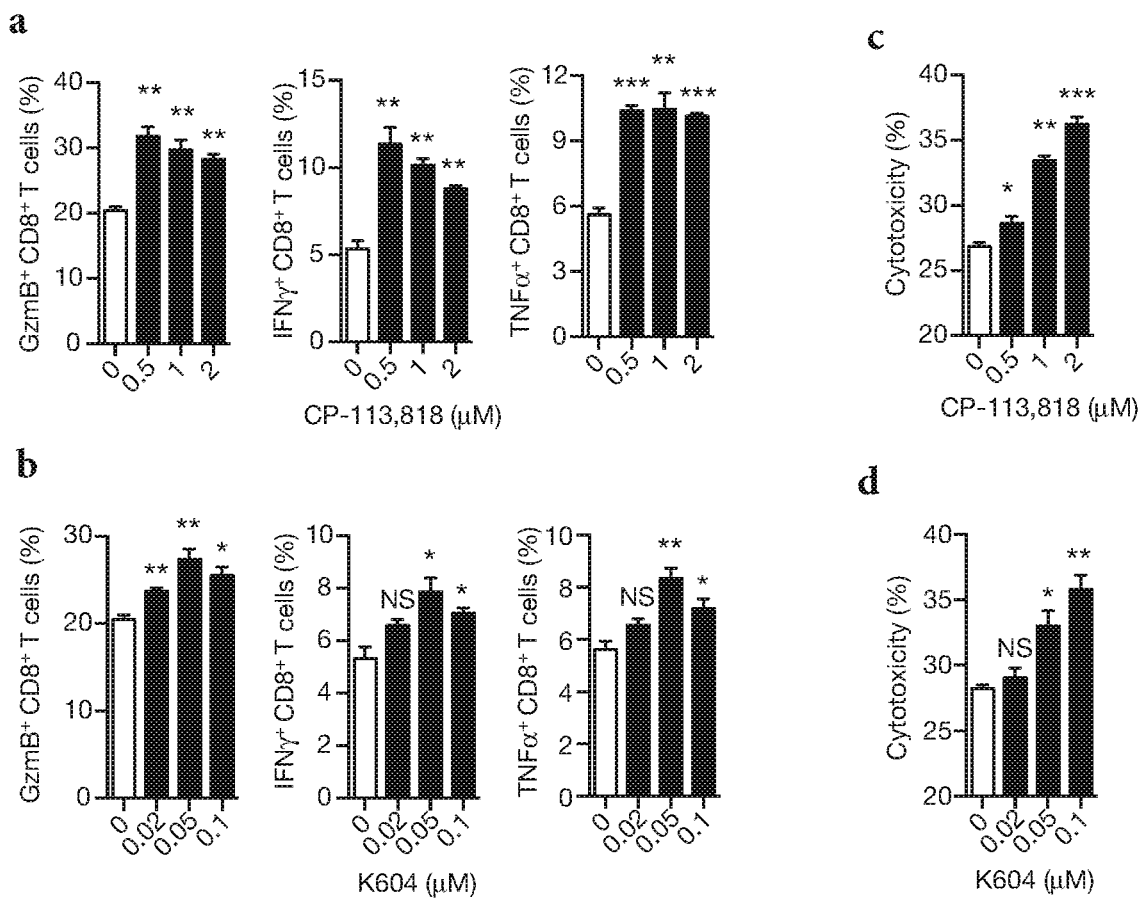
FIG. 1 shows potentiated effector function of CD8+ T cells in response to ACAT1 inhibitors.

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise. The fact that a particular term or phrase is not specifically defined should not be correlated to indefiniteness or lacking clarity, but rather terms herein are used within their ordinary meaning. When trade names are used herein, applicants intend to independently include the trade name product and the active pharmaceutical ingredient(s) of the trade name product.

Recitation of numeric ranges of values throughout the specification is intended to serve as a shorthand notation of referring individually to each separate value falling within the range inclusive of the values defining the range, and each separate value is incorporated in the specification as it were individually recited herein.

Reference to the word "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. The term "about X" thus includes description of "X". In one embodiment, the term "about" includes the indicated amount ±10%. In other embodiments, the term "about" includes the indicated amount ±5%. In certain other embodiments, the term "about" includes the indicated amount ±1%.

As used herein, the terms "subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like. In one embodiment, the subject is a mammal. In one embodiment, the subject is a human.

As used herein, the terms "treating" and "treatment" of a disease include the following: (1) preventing or reducing the risk of developing the disease, i.e., causing the clinical symptoms of the disease not to develop in a subject that may be exposed to or predisposed to the disease but does not yet experience or display symptoms of the disease, (2) inhibiting the disease, i.e., arresting or reducing the development of the disease or its clinical symptoms, and (3) relieving the disease, i.e., causing regression of the disease or its clinical symptoms.

As used herein, the term "administration" or "administer" may refer to administration of an active compound or composition by any route known to one of ordinary skill in the art. Administration can be local or systemic. Examples of "local administration" include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active agents and compounds into implantable devices or constructs, such as vascular stents or other reservoirs, which release the active agents and compounds over extended time intervals for sustained treatment effects. "Systemic administration" includes any route of administration designed to distribute an active compound or composition widely throughout the body via the circulatory system. Thus, systemic administration includes, but is not limited to intra-arterial and intravenous administration. Systemic administration also includes, but is not limited to, oral administration, topical administration, subcutaneous administration, intramuscular administration, transdermal administration, or administration by inhalation, when such administration is directed at absorption and distribution throughout the body by the circulatory system.

As used herein, the term "composition" is intended to mean a combination of active agent and another compound or composition, inert (for example, a detectable agent or label) or active, such as an adjuvant.

As used herein, the term "pharmaceutical composition" is intended to include the combination of an active agent with a carrier, inert or active, making the composition suitable for diagnostic or therapeutic use in vitro, in vivo, or ex vivo.

As used herein, the term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

As used herein, the term "effective amount" or "therapeutically effective amount" means the amount of an active agent or compound described herein that may be effective to elicit the desired biological or medical response. These terms include the amount of an active agent or compound that, when administered to a subject for treating a disease, is sufficient to effect such treatment for the disease. The effective amount will vary depending on the active agent, the disease and its severity and the age, weight, etc., of the subject to be treated.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, adjuvants, excipient, solvent or encapsulating material, involved in carrying or transporting any supplement or composition, or component thereof, from one organ, or portion of the body, to another organ, or portion of the body, or to deliver an agent to the cancerous tissue or a tissue adjacent to the cancerous tissue.

As used herein, the term "formulated" or "formulation" refers to the process in which different chemical substances, including one or more pharmaceutically active ingredients, are combined to produce a dosage form. In one embodiment, two or more pharmaceutically active ingredients can be coformulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "solution" refers to solutions, suspensions, emulsions, drops, ointments, liquid wash, sprays, liposomes which are well known in the art. In one embodiment, the liquid solution contains an aqueous pH buffering agent which resists changes in pH when small quantities of acid or base are added.

As used herein, the term "solvate" refers to an association or complex of one or more solvent molecules and a compound of the disclosure. Examples of solvents that form solvates may include water, isopropanol, ethanol, methanol, dimethylsulfoxide, ethylacetate, acetic acid and ethanolamine.

As used herein, the term "hydrate" refers to the complex formed by the combining of a compound described herein and water.

As used herein, the term "prodrug" refers to compounds disclosed herein that include chemical groups which, in vivo, can be converted and/or can be split off from the remainder of the molecule to provide for the active drug, a pharmaceutically acceptable salt thereof, or a biologically active metabolite thereof.

As used herein, the term "stereoisomer" or "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

As used herein, the term "tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Compounds of a given formula described herein encompass the compound disclosed and all pharmaceutically acceptable salts, esters, stereoisomers, tautomers, prodrugs, hydrate, solvates, and deuterated forms thereof, unless otherwise specified.

The compound names provided herein are named using ChemBioDraw Ultra 12.0. One skilled in the art understands that the compound may be named or identified using various commonly recognized nomenclature systems and symbols. By way of example, the compound may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

As used herein, the term "antibody" includes intact immunoglobulins as well as a number of well-characterized fragments produced by digestion with various peptidases, or genetically engineered artificial antibodies. While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer.

As used herein, the terms "response" or "responsiveness" refers to an anti-cancer response, e.g., in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

As used herein, the term "resistance" or "resistant" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multidrug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In one embodiment, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound or composition of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds and compositions may be further characterized to examine the safety or tolerance dosage in human or non-human subjects. Such properties may be examined using commonly known methods to those skilled in the art.

As used herein, the term "monotherapy" refers to administering a single active agent for treating a condition, such as cancer.

As used herein, the term "combined therapy" refers to treatment of a disease or symptom thereof or a method for achieving a desired physiological change, including administering to an animal, such as a mammal, especially a human being, an effective amount of two or more chemical agents or components to treat the disease or symptom thereof, or to produce the physiological change. In one embodiment, the chemical agents or components disclosed herein are administered together, such as part of the same composition. In another embodiment, the chemical agents or components disclosed herein are administered separately and independently at the same time or at different times (e.g., administration of each agent or component is separated by a finite period of time from each other).

As used herein, the terms "synergy" and "synergistic effect" encompass a more than additive effect of two or more agents compared to their individual effects. In one embodiment, synergy or synergistic effect refers to an advantageous effect of using two or more agents in combination, e.g., in a pharmaceutical composition, or in a method of treatment. A synergistic effect may be attained when the active ingredients are: (1) coformulated and administered or delivered simultaneously in a combined formulation; (2) delivered by alternation or in parallel as separate formulations; or (3) by some other regimen. When delivered in alternation therapy, a synergistic effect may be attained when the active agents or compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients may be administered together.

As used herein, the term "immune cell therapy" or "adoptive cell therapy" refers to the passive transfer of ex vivo grown cells, most commonly immune-derived cells, into a host with the goal of transferring the immunologic functionality and characteristics of the transplant. Adoptive cell transfer can be autologous and/or allogenic T cells. Adoptive T cell transfer therapy refers to a form of transfusion therapy comprising the infusion of various mature T cell subsets with the goal of eliminating a tumor and preventing its recurrence, for example. There are many forms of adoptive T cell therapy being used for cancer treatment, including: culturing tumor infiltrating lymphocytes (TIL), isolating and expanding one particular T cell or clone, and even using T cells that have been engineered to potently recognize and attack tumors.

Cancer Treatment By Inhibiting ACAT1

Reactivating the cytotoxicity of $CD8^+$ T cells is of great clinical interest in cancer immunotherapy. It is a surprising and unexpected finding of the present inventors that the antitumor response of $CD8^+$ T cells can be potentiated by modulating cholesterol metabolism. Inhibiting cholesterol esterification in T cells by genetic ablation or pharmacological inhibition of ACAT1 (acyl-coenzyme A:cholesterol acyltransferases 1), a key cholesterol esterification enzyme, led to potentiated effector function and enhanced proliferation of $CD8^+$ T cells but not $CD4^+$ T cells. This is attributed to the elevation of the plasma membrane cholesterol level of $CD8^+$ T cells that causes enhanced T-cell receptor clustering and signaling as well as more efficient formation of immunological synapse. ACAT1-deficient CD8+ T cells showed better effect in controlling melanoma growth and metastasis in mice than wild-type CD8+ T cells.

Avasimibe, an ACAT inhibitor tested in clinical trials for treating atherosclerosis and showed good human safety profile, was used to treat melanoma and exhibited good antitumor effect. ACAT1, an established target for atherosclerosis, is therefore a potential target for cancer immunotherapy as well.

In one embodiment, therefore, provided is a method for treating a cancer in a patient. The method, in one embodiment, entails administering to the patient a therapeutically effective amount of an acyl-coenzyme A:cholesterol acyl-transferases 1 (ACAT1) inhibitor.

Cancer Patients

In one embodiment, the cancer is carcinoma, sarcoma, melanoma, lymphoma or leukemia. In some variations, the cancer is cancers of the rhinal, nasal sinuses, nasopharynx, tongue, mouth, pharynx, throat, sialisterium, and oral cavity, esophageal cancer, stomach cancer, cardia cancer, mediastinum cancer, gastrointestinal stromal tumor, cancer of the small intestine, anal cancer, cancer of the anal canal, ano-rectal cancer, liver cancer, intrahepatic bile duct cancer, gallbladder cancer, biliary cancer, pancreatic cancer, cancer of other digestive organs, cancer of the larynx, osteosarcoma, bone and joint cancer, rhabdomyosarcoma, synovial sarcoma, Ewing's sarcoma, fibrous histiocytoma, uterine cancer, cervical cancer, uterine corpus cancer, cancer of the vulva, vaginal cancer, endometrial cancer, ovarian cancer, testicular cancer, penile cancer, prostate cancer, urinary bladder cancer, kidney cancer, renal cancer, cancer of the ureter and other urinary organs, ocular cancer, brain and nervous system cancer, (central nervous system) CNS cancers, thyroid cancer, leukemia, myeloma, melanoma, soft tissue sarcoma, or lymphoma. In one embodiment, the cancer is melanoma or lung cancer.

In some embodiments, the cancer is selected from the group consisting of melanoma, lymphoma, esophageal cancer, liver cancer, head and neck cancer, bladder cancer, endometrial cancer, kidney cancer, thyroid cancer, breast cancer, colorectal cancer, leukemia, lung cancer, pancreatic cancer, and prostate cancer.

In some embodiments, the cancer is selected from the group consisting of melanoma, lymphoma, esophageal cancer, liver cancer, head and neck cancer, bladder cancer, endometrial cancer, kidney cancer and thyroid cancer.

In some embodiments, the cancer is melanoma. In some embodiments, the melanoma is selected from the group consisting of Lentigo maligna, Lentigo maligna melanoma, superficial spreading melanoma, acral lentiginous melanoma, mucosal melanoma, nodular melanoma, polyploid melanoma, desmoplastic melanoma, amelanotic melanoma, and soft-tissue melanoma.

In some embodiments, the ACAT1 inhibitor is not cytotoxic against the cancer cells directly. Rather, the ACAT1 can activate a CD8+ T cell which exhibits antitumor activity. The responsiveness of the cancer to the ACAT1 inhibitor can be tested with methods known in the art, such as in vitro cytotoxicity assays, in the absence of immune cells, such as CD8+ cell. Examples of such cancers include, without limitation, some or all of melanoma, lymphoma, esophageal cancer, liver cancer, head and neck cancer, bladder cancer, endometrial cancer, kidney cancer and thyroid cancer.

In some embodiments, the cancer patient that has a suppressed CD8+ T cell in a tumor microenvironment. As used herein, the term "CD8+ T cells" refer to CD8 positive cells. CD8+ T cells express CD8 on the cells' surface, and are also referred to as cytotoxic T cells. As used herein, the term "cytotoxic T lymphocyte" or "CTL" may refer to cytotoxic T cells that express T-cell receptors (TCRs) that can recognize a specific antigen capable of stimulating an immune response. Such antigen may be produced by cancer cells or viruses.

The term "suppressed CD8+ T cell" refers to a CD8+ T cell in a subject or a tissue (a tumor tissue) in a subject that has reduced immune response as compared to a control subject (e.g., a healthy individual) or a control tissue (e.g., a normal tissue).

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

In some embodiments, the suppressed CD8+ T cell has reduced cytotoxic activity, reduced proliferative activity or reduced infiltration activity as compared to a CD8+ T cell not in the tumor microenvironment.

The treatment can be suitable for cancer of different stages. In some embodiments, the cancer patient has a stage I, II, III, or IV cancer. In one embodiment, the cancer patient has a stage I cancer. Stage 1 usually means that a cancer is relatively small and contained within the organ it started in. Stage 2 usually means the cancer has not started to spread into surrounding tissue but the tumor is larger than in stage 1. Sometimes stage 2 means that cancer cells have spread into lymph nodes close to the tumor. This depends on the particular type of cancer. Stage 3 usually means the cancer is larger. It may have started to spread into surrounding tissues and there are cancer cells in the lymph nodes in the area. Stage 4 means the cancer has spread from where it started to another body organ. This is also called secondary or metastatic cancer.

In some embodiments, the patient does not have a tumor tissue having a diameter of at least 2 cm, or alternatively 1.9 cm, 1.8 cm, 1.7 cm, 1.6 cm, 1.5 cm, 1.4 cm, 1.3 cm, 1.2 cm, 1.1 cm, 1 cm, 0.9 cm, 0.8 cm, 0.7 cm, 0.6 cm, 0.5 cm, 0.4 cm, 0.3 cm, 0.2 cm or 0.1 cm.

In some embodiments, the cancer patient does not have a tumor tissue with activated angiogenesis. Cancer cells are cells that have lost their ability to divide in a controlled fashion. A malignant tumor consists of a population of rapidly dividing and growing cancer cells that progressively accrues mutations. However, tumors need a dedicated blood supply to provide the oxygen and other essential nutrients they require in order to grow beyond a certain size (generally 1-2 $mm^3$).

In one embodiment, provided herein is a method for treating a human who exhibits one or more symptoms associated with cancer. In one embodiment, the human is at an early stage of cancer. In other embodiments, the human is at an advanced stage of cancer.

In one embodiment, provided herein is a method for treating a human who is undergoing one or more standard therapies for treating cancer, such as chemotherapy, radiotherapy, immunotherapy, and/or surgery. Thus, in some foregoing embodiments, the ACAT1 inhibitor, as disclosed herein, may be administered before, during, or after administration of chemotherapy, radiotherapy, immunotherapy, and/or surgery.

In another aspect, provided herein is a method for treating a human who is "refractory" to a cancer treatment or who is in "relapse" after treatment for cancer. A subject "refractory" to an anti-cancer therapy means they do not respond to the particular treatment, also referred to as resistant. The cancer may be resistant to treatment from the beginning of treatment, or may become resistant during the course of treatment, for example after the treatment has shown some effect on the cancer, but not enough to be considered a remission or partial remission. A subject in "relapse" means that the cancer has returned or the signs and symptoms of cancer have returned after a period of improvement, e.g., after a treatment has shown effective reduction in the cancer, such as after a subject is in remission or partial remission.

In some variations, the human is (i) refractory to at least one anti-cancer therapy, or (ii) in relapse after treatment with at least one anti-cancer therapy, or both (i) and (ii). In one embodiment, the human is refractory to at least two, at least three, or at least four anti-cancer therapies (including, for example, standard or experimental chemotherapies).

In another aspect, provided is a method for sensitizing a human who is (i) refractory to at least one chemotherapy treatment, or (ii) in relapse after treatment with chemotherapy, or both (i) and (ii), wherein the method comprises administering an ACAT1 inhibitor, with or without an anti-tumor agent, as disclosed herein, to the human in need thereof. A human who is sensitized is a human who is responsive to the treatment involving administration of an ACAT1 inhibitor with or without an antitumor agent, as disclosed herein, or who has not developed resistance to such treatment.

In another aspect, provided herein is a methods for treating a human for a cancer, with comorbidity, wherein the treatment is also effective in treating the comorbidity. A "comorbidity" to cancer is a disease that occurs at the same time as the cancer.

ACAT1 Inhibitors

As used herein, the term "ACAT1 inhibitor" may refer to any agent that inhibits activity or expression of ACAT1. In an embodiment, ACAT1 inhibitor may demonstrate in vitro or in vivo binding affinity for ACAT1 such that the normal activity of the ACAT1 enzyme is reduced or eliminated. In one embodiment, an ACAT1 inhibitor disclosed herein can inhibit ACAT1 selectively. In one embodiment, an ACAT1 inhibitor can inhibit both isoforms of the ACAT enzyme, ACAT1 and ACAT2. In one embodiment, an ACAT1 inhibitor disclosed herein can have affinity for other targets (enzymes or receptors) besides ACAT1. In one embodiment, ACAT1 inhibitors disclosed herein may inhibit enzymatic activity of ACAT1 by at least 10%, at least 30%, at least 50%, at least 70%, or at least 90%. In one embodiment, ACAT1 inhibitors disclosed herein may inhibit gene expression or translation of ACAT1. In one embodiment, the ACAT1 inhibitor is selected from a group consisting of a small inhibitory RNA (siRNA), a small hairpin RNA (shRNA), a microRNA (miRNA), or an anti-sense nucleic acid, (B) an ACAT1 inhibitory antibody or fragment thereof, (C) a small molecule inhibitor, and combinations thereof.

Non-limiting examples of ACAT1 inhibitors avasimibe (CI-1011), pactimibe, purpactins, manassantin A, diphenylpyridazine derivatives, glisoprenin A, CP113,818, K604, beauveriolide I, beauveriolide III, U18666A, TMP-153, YM750, GERI-BP002-A, Sandoz Sah 58-035, VULM 1457, Lovastatin, CI976, CL-283,546, CI-999, E5324, YM17E, FR182980, ATR-101 (PD132301 or PD132301-2), F-1394, HL-004, F-12511 (eflucimibe), cinnamic acid derivatives, cinnamic derivative, Dup 128, RP-73163, pyripyropene C, FO-1289, AS-183, SPC-15549, FO-6979, Angekica, ginseng, Decursin, terpendole C, beauvericin, spylidone, pentacecilides, CL-283,546, betulinic acid, shikonin derivatives, esculeogenin A, Wu-V-23, pyripyropene derivatives A, B, and D, glisoprenin B-D, saucerneol B, sespendole, diethyl pyrocarbonate, beauveriolide analogues, Acaterin, DL-melinamide, PD 138142-15, CL277,082, EAB-309, Enniatin antibiotics, Epi-cochlioquinone A, FCE-27677, FR186485, FR190809, NTE-122, obovatol, panaxadiols, protopanaxadiols, polyacetylenes, SaH 57-118, AS-186, BW-447A, 447C88, T-2591, TEI-6522, TEI-6620, XP 767, XR 920, GERI-BP001, gomisin N, gypsetin, helminthosporol, TS-962, isochromophilones, kudingosides, lateritin, naringenin, and combinations thereof. In one example, the ACAT1 inhibitor is avasimibe. In one example, the ACAT1 inhibitor is K604. In one example, the ACAT1 inhibitor is CP113,818.

For example, the ACAT1 inhibitor can be avasimibe:

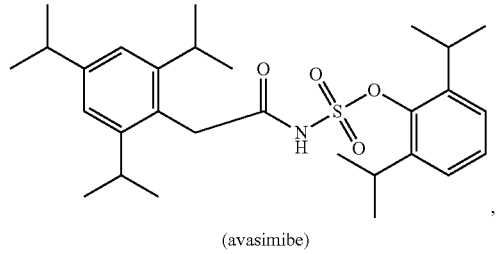 [SMILES: CC(C)c1cc(C(C)C)c(CC(=O)NS(=O)(=O)Oc2c(C(C)C)cccc2C(C)C)c(C(C)C)c1]

(avasimibe)

or a pharmaceutically acceptable salt, solvate, prodrug, stereoisomer, mixture of stereoisomers or hydrate thereof.

In addition to the chemical structure, avasimibe may also be referred to or identified as [2,6-di(propan-2-yl)phenyl] N-[2-[2,4,6-tri(propan-2-yl)phenyl]acetyl]sulfamate, or CI-1011. Avasimibe is an ACAT inhibitor that was tested in clinical trials for treating atherosclerosis and showed good human safety profile. This compound was discontinued in Phase III clinical trials for treatment of atherosclerosis. Avasimibe has been shown to be well tolerated by adult human subjects at doses at least up to 750 mg four times daily (i.e., 3000 mg/day). See Kharbanda et al (2005) Circulation 111:804-807.

In one embodiment, the ACAT1 inhibitor can be K604:

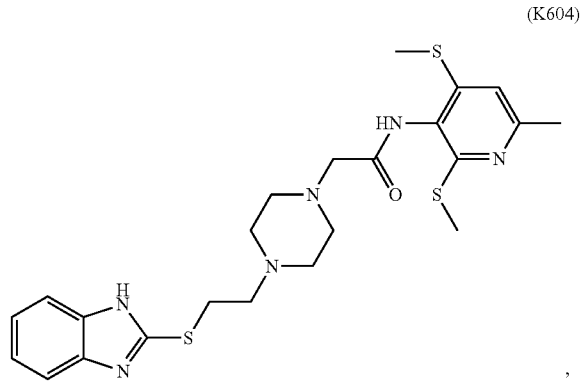 [SMILES: CSc1cc(C)nc(SC)c1NC(=O)CN1CCN(CCSc2nc3ccccc3[nH]2)CC1]

(K604)

or a pharmaceutically acceptable salt, solvate, prodrug, stereoisomer, mixture of stereoisomers or hydrate thereof.

In addition to the chemical structure, K604 may also be referred to or identified as 2-[4-[2-(benzimidazol-2-ylthio) ethyl] piperazin-1yl]-N-[2,4-bis(methylthio)-6-methyl-3-pyridyl]acetamide.

In one embodiment, the ACAT1 inhibitor can be CP-113,818:

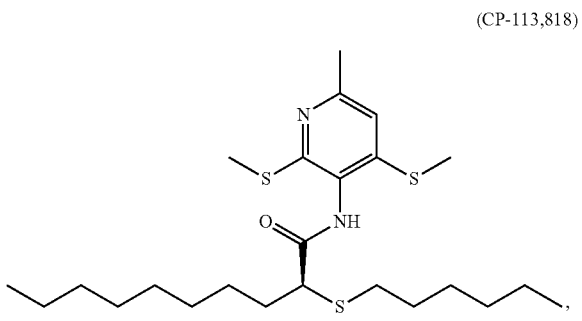 [SMILES: CCCCCCCC[C@H](SCCCCCC)C(=O)Nc1c(SC)cc(C)nc1SC]
(CP-113,818)

or a pharmaceutically acceptable salt, solvate, prodrug, stereoisomer, mixture of stereoisomers or hydrate thereof.

In addition to the chemical structure, CP-113,818 may also be referred to or identified as 2-(hexylthio)-N-(6-(methyl-2,4-bis(methylthio)-3-pyridinyl)-, (S)—N-(2,4-Bis(methylthio)-6-methylpyridin-3-yl)-2-(hexylthio)decanoic acid amide, or decanamide.

In one embodiment, the ACAT1 inhibitor can be CI 976:

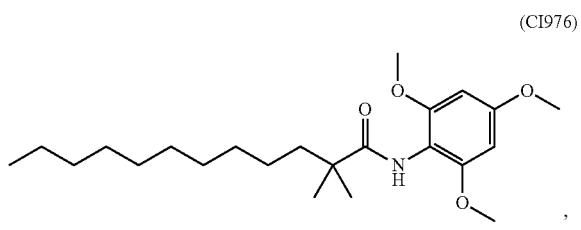 [SMILES: CCCCCCCCCCC(C)(C)C(=O)Nc1c(OC)cc(OC)cc1OC]
(CI976)

or a pharmaceutically acceptable salt, solvate, prodrug, stereoisomer, mixture of stereoisomers or hydrate thereof.

In addition to the chemical structure, CI 976 may also be referred to or identified as 2,2-dimethyl-n-(2,4,6-trimethoxyphenyl)-dodecanamide, CI 976, PD 128042, or N-(2,4,6-Trimethoxyphenyl)-2,2-dimethyldodecanamide.

In one embodiment, the ACAT1 inhibitor can be TMP-153:

(TMP-153)
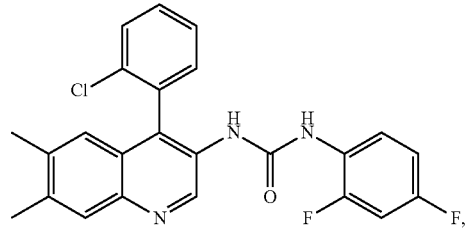

or a pharmaceutically acceptable salt, solvate, prodrug, stereoisomer, mixture of stereoisomers or hydrate thereof.

In addition to the chemical structure, TMP-153 may also be referred to or identified as N-[4-(2-chlorophenyl)-6,7-dimethyl-3-quinolinyl]-N'-(2,4-difluorophenyl)-urea.

In one embodiment, the ACAT1 inhibitor can be YM 750:

(YM 750)
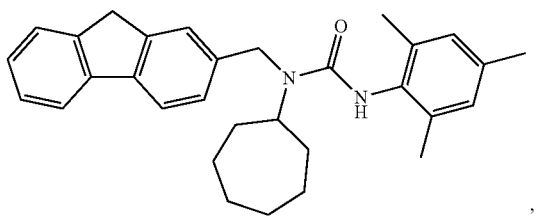

or a pharmaceutically acceptable salt, solvate, prodrug, stereoisomer, mixture of stereoisomers or hydrate thereof.

In addition to the chemical structure, YM 750 may also be referred to or identified as N-Cycloheptyl-N-(9H-fluoren-2-ylmethyl)-N'-(2,4,6-trimethylphenyl)urea.

In one embodiment, the ACAT1 inhibitor can be GERI-BP002-A:

(GERI-BP002-A)
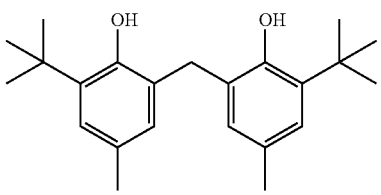

or a pharmaceutically acceptable salt, solvate, prodrug, stereoisomer, mixture of stereoisomers or hydrate thereof.

In addition to the chemical structure, GERI-BP002-A may also be referred to or identified as 2,2'-methylenebis(6-tert-butyl-4-methylphenol).

In one embodiment, the ACAT1 inhibitor can be Sandoz 58-035:

(Sandoz 58-035)
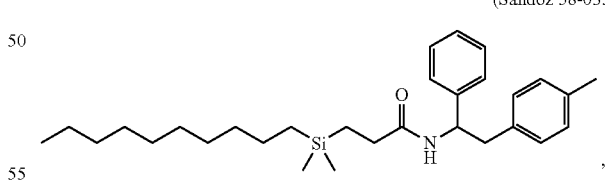

or a pharmaceutically acceptable salt, solvate, prodrug, stereoisomer, mixture of stereoisomers or hydrate thereof.

In addition to the chemical structure, Sandoz 58-035 may also be referred to or identified as 3-[decyldimethylsilyl]-n-[2-(4-methylphenyl)-1-phenethyl]propanamide or SA 58-035.

In one embodiment, the ACAT1 inhibitor can be VULM 1457:

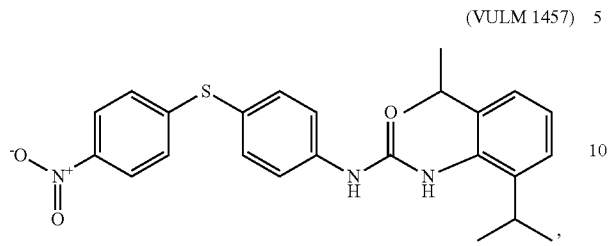

(VULM 1457)

or a pharmaceutically acceptable salt, solvate, prodrug, stereoisomer, mixture of stereoisomers or hydrate thereof.

In addition to the chemical structure, VUML 1457 may also be referred to or identified as n-[2,6-bis(1-methylethyl)phenyl]-n'-[4-[(4-nitrophenyl)thio]phenyl]urea.

In one embodiment, the ACAT1 inhibitor can be ATR-101:

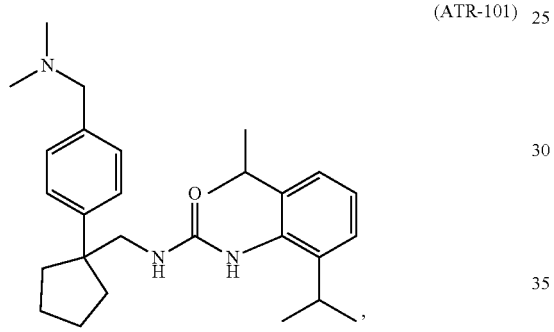

(ATR-101)

or a pharmaceutically acceptable salt, solvate, prodrug, stereoisomer, mixture of stereoisomers or hydrate thereof.

In addition to the chemical structure, ATR-101 may also be referred to or identified as N-(2,6-bis(isopropyl)phenyl)-N'-((1-(4-(dimethylaminomethyl)phenyl)cyclopentyl)methyl)urea.

In one embodiment, the ACAT1 inhibitor can be beauveriolide I:

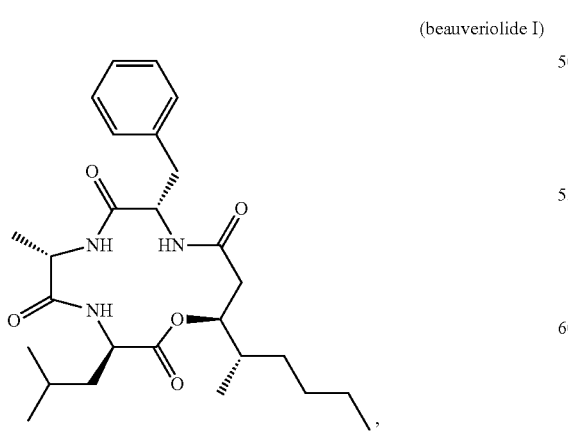

(beauveriolide I)

or a pharmaceutically acceptable salt, solvate, prodrug, stereoisomer, mixture of stereoisomers or hydrate thereof.

In addition to the chemical structure, beauveriolide I may also be referred to or identified as (3R,6S,9S,13S)-9-benzyl-13-[(2S)-hexan-2-yl]-6-methyl-3-(2-methylpropyl)-1-oxa-4,7,10-triazacyclotridecane-2,5,8,11-tetrone.

In one embodiment, the ACAT1 inhibitor can be beauveriolide III:

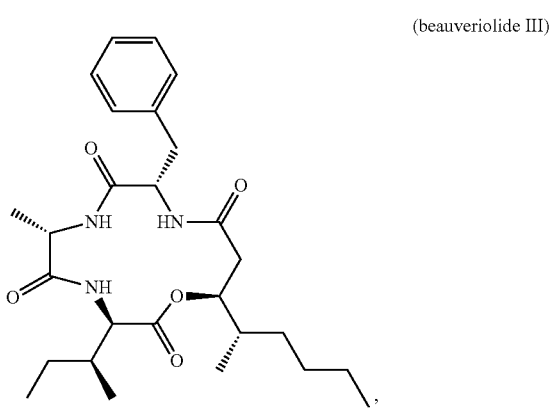 [SMILES: CCCC[C@H](C)[C@@H]1CC(=O)N[C@@H](Cc2ccccc2)C(=O)N[C@@H](C)C(=O)N[C@H]([C@@H](C)CC)C(=O)O1]

(beauveriolide III)

or a pharmaceutically acceptable salt, solvate, prodrug, stereoisomer, mixture of stereoisomers or hydrate thereof.

In addition to the chemical structure, beauveriolide III may also be referred to or identified as (3R,6S,9S,13S)-9-benzyl-3-[(2S)-butan-2-yl]-13-[(2S)-hexan-2-yl]-6-methyl-1-oxa-4,7,10-triazacyclotridecane-2,5,8,11-tetrone.

In one embodiment, the ACAT1 inhibitor can be pactimibe:

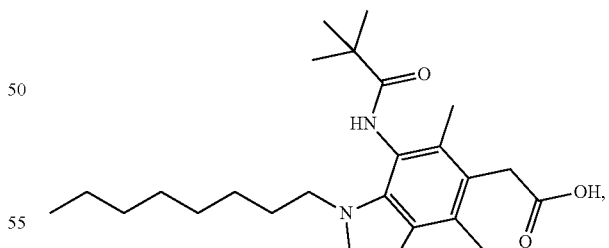

(pactimibe)

or a pharmaceutically acceptable salt, solvate, prodrug, stereoisomer, mixture of stereoisomers or hydrate thereof.

In addition to the chemical structure, pactimibe may also be referred to or identified as 2-[7-(2,2-dimethylpropanoylamino)-4,6-dimethyl-1-octyl-2,3-dihydroindol-5-yl]acetic acid.

In one embodiment, the ACAT1 inhibitor can be eflucimibe:

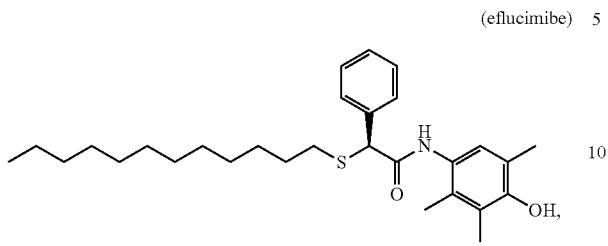

(eflucimibe)

or a pharmaceutically acceptable salt, solvate, prodrug, stereoisomer, mixture of stereoisomers or hydrate thereof.

In addition to the chemical structure, eflucimibe may also be referred to or identified as (2S)-2-dodecylsulfanyl-N-(4-hydroxy-2,3,5-trimethylphenyl)-2-phenylacetamide, F 12511, or F-12511.

In some embodiments, the ACAT1 inhibitor is conjugated to a targeting molecule that recognizes the CD8+ T cell. The targeting molecule can be an antibody or fragment thereof that specifically recognizes a marker on the CD8+ T cell. A non-limiting example of the marker is CD8.

Combination Therapies

It is discovered herein that the combination of an ACAT1 inhibitor and another antitumor agent (e.g., dacarbazine) resulted in superior growth inhibition in certain cancer models, demonstrating that such combinations provide broader and superior efficacies in cancer treatments.

In accordance with one embodiment of the disclosure, therefore, provided is a composition that includes an ACAT1 inhibitor and a second anticancer (chemotherapeutic) agent (e.g., dacarbazine). Chemotherapeutic agents may be categorized by their mechanism of action into, for example, the following groups:

- anti-metabolites/anti-cancer agents such as pyrimidine analogs floxuridine, capecitabine, and cytarabine;
- purine analogs, folate antagonists, and related inhibitors;
- antiproliferative/antimitotic agents including natural products such as *vinca* alkaloid (vinblastine, vincristine) and microtubule such as taxane (paclitaxel, docetaxel), vinblastin, nocodazole, epothilones, vinorelbine (NAVELBINE®), and epipodophyllotoxins (etoposide, teniposide);
- DNA damaging agents such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, mechlorethamine, mitomycin, mitoxantrone, nitrosourea, procarbazine, taxol, taxotere, teniposide, etoposide, and triethylenethiopho sphoramide;
- antibiotics such as dactinomycin, daunorubicin, doxorubicin, idarubicin, anthracyclines, mitoxantrone, bleomycins, plicamycin (mithramycin), and mitomycin;
- enzymes such as L-asparaginase which systemically metabolizes L-asparagine and deprives cells which do not have the capacity to synthesize their own asparagine;
- antiplatelet agents;
- antiproliferative/antimitotic alkylating agents such as nitrogen mustards cyclophosphamide and analogs (melphalan, chlorambucil, hexamethylmelamine, and thiotepa), alkyl nitrosoureas (carmustine) and analogs, streptozocin, and triazenes (dacarbazine);
- antiproliferative/antimitotic antimetabolites such as folic acid analogs (methotrexate);
- platinum coordination complexes (cisplatin, oxiloplatinim, and carboplatin), procarbazine, hydroxyurea, mitotane, and aminoglutethimide;
- hormones, hormone analogs (estrogen, tamoxifen, goserelin, bicalutamide, and nilutamide), and aromatase inhibitors (letrozole and anastrozole);
- anticoagulants such as heparin, synthetic heparin salts, and other inhibitors of thrombin;
- fibrinolytic agents such as tissue plasminogen activator, streptokinase, urokinase, aspirin, dipyridamole, ticlopidine, and clopidogrel;
- antimigratory agents;
- antisecretory agents (breveldin);
- immunosuppressives tacrolimus, sirolimus, azathioprine, and mycophenolate;
- compounds (TNP-470, genistein) and growth factor inhibitors (vascular endothelial growth factor inhibitors and fibroblast growth factor inhibitors);
- angiotensin receptor blockers, nitric oxide donors;
- anti-sense oligonucleotides;
- antibodies such as trastuzumab and rituximab;
- cell cycle inhibitors and differentiation inducers such as tretinoin;
- inhibitors, topoisomerase inhibitors (doxorubicin, daunorubicin, dactinomycin, eniposide, epirubicin, etoposide, idarubicin, irinotecan, mitoxantrone, topotecan, and irinotecan), and corticosteroids (cortisone, dexamethasone, hydrocortisone, methylprednisolone, prednisone, and prednisolone);
- growth factor signal transduction kinase inhibitors;
- dysfunction inducers;
- toxins such as Cholera toxin, ricin, Pseudomonas exotoxin, *Bordetella pertussis* adenylate cyclase toxin, diphtheria toxin, and caspase activators;
- and chromatin.

Further examples of chemotherapeutic agents include:
- alkylating agents such as thiotepa and cyclophosphamide (CYTOXAN®);
- alkyl sulfonates such as busulfan, improsulfan, and piposulfan;
- aziridines such as benzodopa, carboquone, meturedopa, and uredopa;
- emylerumines and memylamelamines including alfretamine, triemylenemelamine, triethylenephosphoramide, triethylenethiophosphoramide, and trimemylolomelamine;
- acetogenins, especially bullatacin and bullatacinone;
- a camptothecin, including synthetic analog topotecan;
- bryostatin;
- callystatin;
- CC-1065, including its adozelesin, carzelesin, and bizelesin synthetic analogs;
- cryptophycins, particularly cryptophycin 1 and cryptophycin 8;
- dolastatin;
- duocarmycin, including the synthetic analogs KW-2189 and CBI-TMI;
- eleutherobin;
- pancratistatin;
- a sarcodictyin;
- spongistatin;
- nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, and uracil mustard;

nitrosoureas such as carmustine, chlorozotocin, foremustine, lomustine, nimustine, and ranimustine;

antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin;

anti-metabolites such as methotrexate and 5-fluorouracil (5-FU);

folic acid analogs such as demopterin, methotrexate, pteropterin, and trimetrexate;

purine analogs such as fludarabine, 6-mercaptopurine, thiamiprine, and thioguanine;

pyrimidine analogs such as ancitabine, azacitidine, 6-azauridine, carmofur, cytarabine, dideoxyuridine, doxifluridine, enocitabine, and floxuridine;

androgens such as calusterone, dromostanolone propionate, epitiostanol, mepitiostane, and testolactone;

anti-adrenals such as aminoglutethimide, mitotane, and trilostane;

folic acid replinishers such as frolinic acid;

trichothecenes, especially T-2 toxin, verracurin A, roridin A, and anguidine;

taxoids such as paclitaxel (TAXOL®) and docetaxel (TAXOTERE®);

platinum analogs such as cisplatin and carboplatin;

aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); Ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; FOLFIRI (fluorouracil, leucovorin, and irinotecan);

and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include flutamide, nilutamide, bicalutamide, leuprohde, and goserelin.

Examples of chemotherapeutic agents also include anti-angiogenic agents including, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs ((l-azetidine-2-carboxylic acid (LACA)), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, and metalloproteinase inhibitors such as BB-94. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Examples of chemotherapeutic agents also include antifibrotic agents including, but are not limited to, the compounds such as beta-aminoproprionitrile (BAPN), as well as the compounds disclosed in U.S. Pat. No. 4,965,288 (Palfreyman, et al.) relating to inhibitors of lysyl oxidase and their use in the treatment of diseases and conditions associated with the abnormal deposition of collagen and U.S. Pat. No. 4,997,854 (Kagan et al.) relating to compounds which inhibit LOX for the treatment of various pathological fibrotic states, which are herein incorporated by reference. Further exemplary inhibitors are described in U.S. Pat. No. 4,943,593 (Palfreyman et al.) relating to compounds such as 2-isobutyl-3-fluoro-, chloro-, or bromo-allylamine, U.S. Pat. No. 5,021,456 (Palfreyman et al.), U.S. Pat. No. 5,059,714 (Palfreyman et al.), U.S. Pat. No. 5,120,764 (Mccarthy et al.), U.S. Pat. No. 5,182,297 (Palfreyman et al.), U.S. Pat. No. 5,252,608 (Palfreyman et al.) relating to 2-(1-naphthyloxymemyl)-3-fluoroallylamine, and U.S. Pub. No.: 2004/0248871 (Farjanel et al.), which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiolsulphanate, and sodium-4-mercaptobutanesulphinate trihydrate.

Examples of chemotherapeutic agents also include immunotherapeutic agents including and are not limited to therapeutic antibodies suitable for treating patients. Some examples of therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90, or iodine-131.

In a one embodiment, the additional therapeutic agent is a nitrogen mustard alkylating agent. Nonlimiting examples of nitrogen mustard alkylating agents include chlorambucil.

In one embodiment, the compounds and compositions described herein may be used or combined with one or more additional therapeutic agents. The one or more therapeutic agents include, but are not limited to, an inhibitor of Abl, activated CDC kinase (ACK), adenosine A2B receptor (A2B), apoptosis signal-regulating kinase (ASK), Auroa kinase, Bruton's tyrosine kinase (BTK), BET-bromodomain (BRD) such as BRD4, c-Kit, c-Met, CDK-activating kinase (CAK), calmodulin-dependent protein kinase (CaMK), cyclin-dependent kinase (CDK), casein kinase (CK), discoidin domain receptor (DDR), epidermal growth factor receptors (EGFR), focal adhesion kinase (FAK), Flt-3, FYN, glycogen synthase kinase (GSK), HCK, histone deacetylase (HDAC), IKK such as IKKβε, isocitrate dehydrogenase (IDH) such as IDH1, Janus kinase (JAK), KDR, lymphocyte-specific protein tyrosine kinase (LCK), lysyl oxidase protein, lysyl oxidase-like protein (LOXL), LYN, matrix metalloprotease (MMP), MEK, mitogen-activated protein kinase (MAPK), NEK9, NPM-ALK, p38 kinase, platelet-derived growth factor (PDGF), phosphorylase kinase (PK), polo-like kinase (PLK), phosphatidylinositol 3-kinase (PI3K), protein kinase (PK) such as protein kinase A, B, and/or C, PYK, spleen tyrosine kinase (SYK), serine/threonine kinase TPL2, serine/threonine kinase STK, signal transduction and transcription (STAT), SRC, serine/threonine-protein kinase (TBK) such as TBK1, TIE, tyrosine kinase (TK), vascular endothelial growth factor receptor (VEGFR), YES, or any combination thereof.

ASK inhibitors include ASK1 inhibitors. Examples of ASK1 inhibitors include, but are not limited to, those described in WO 2011/008709 (Gilead Sciences) and WO 2013/112741 (Gilead Sciences).

Examples of BTK inhibitors include, but are not limited to, ibrutinib, HM71224, ONO-4059, and CC-292.

DDR inhibitors include inhibitors of DDR1 and/or DDR2. Examples of DDR inhibitors include, but are not limited to, those disclosed in WO 2014/047624 (Gilead Sciences), US 2009/0142345 (Takeda Pharmaceutical), US 2011/0287011 (Oncomed Pharmaceuticals), WO 2013/027802 (Chugai Pharmaceutical), and WO 2013/034933 (Imperial Innovations).

Examples of HDAC inhibitors include, but are not limited to, pracinostat and panobinostat.

JAK inhibitors inhibit JAK1, JAK2, and/or JAK3. Examples of JAK inhibitors include, but are not limited to, filgotinib, ruxolitinib, fedratinib, tofacitinib, baricitinib, lestaurtinib, pacritinib, XL019, AZD1480, INCB039110, LY2784544, BMS911543, and NS018.

LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences).

Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

MMP inhibitors include inhibitors of MMP1 through 10. Examples of MMP9 inhibitors include, but are not limited to, marimastat (BB-2516), cipemastat (Ro 32-3555), and those described in WO 2012/027721 (Gilead Biologics).

PI3K inhibitors include inhibitors of PI3Kγ, PI3Kδ, PI3Kβ, PI3Kα, and/or pan-PI3K. Examples of PI3K inhibitors include, but are not limited to, wortmannin, BKM120, CH5132799, XL756, and GDC-0980.

Examples of PI3Kγ inhibitors include, but are not limited to, ZSTK474, AS252424, LY294002, and TG100115.

Examples of PI3Kδ inhibitors include, but are not limited to, PI3K II, TGR-1202, AMG-319, GSK2269557, X-339, X-414, RP5090, KAR4141, XL499, OXY111A, IPI-145, IPI-443, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Examples of PI3Kβ inhibitors include, but are not limited to, GSK2636771, BAY 10824391, and TGX221.

Examples of PI3Kα inhibitors include, but are not limited to, buparlisib, BAY 80-6946, BYL719, PX-866, RG7604, MLN1117, WX-037, AEZA-129, and PA799.

Examples of pan-PI3K inhibitors include, but are not limited to, LY294002, BEZ235, XL147 (SAR245408), and GDC-0941.

Examples of SYK inhibitors include, but are not limited to, tamatinib (R406), fostamatinib (R788), PRT062607, BAY-61-3606, NVP-QAB 205 AA, R112, R343, and those described in U.S. Pat. No. 8,450,321 (Gilead Conn.).

TKIs may target epidermal growth factor receptors (EGFRs) and receptors for fibroblast growth factor (FGF), platelet-derived growth factor (PDGF), and vascular endothelial growth factor (VEGF). Examples of TKIs that target EGFR include, but are not limited to, gefitinib and erlotinib. Sunitinib is a non-limiting example of a TKI that targets receptors for FGF, PDGF, and VEGF.

In one embodiment, the chemotherapeutic agent is an alkylating antineoplastic agent, such as those having a triazene structure (e.g., dacarbazine, mitozolomide and temozolomide). Dacarbazine is a member of the class of alkylating agents, which destroy cancer cells by adding an alkyl group ($C_nH_{2n+1}$) to its DNA. Dacarbazine is the monotherapeutic drug of choice in the treatment of patients having metastatic melanoma without metastases to the central nervous system (CNS). The structure of dacarbazine is as follows:

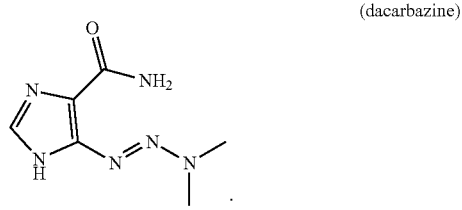
(dacarbazine)

In addition to the chemical structure, dacarbazine may also be referred to or identified as 5-(3,3-Dimethyl-1-triazenyl)imidazole-4-carboxamide, dimethyl-triazen imidazole carboxamide, DTIC, DTIC-Dome, DIC, or imidazole carboxamide.

Treatment Methods and Uses

The present disclosure, in one embodiment, provides a method for treating cancer in a human in need thereof, comprising administering to the human a therapeutically effective amount of an ACAT1 inhibitor. In one embodiment, provided is a method for treating cancer in a human in need thereof, comprising administering to the human a therapeutically effective amount of an ACAT1 inhibitor and a therapeutically effective amount of an antitumor agent (e.g., an immune checkpoint inhibitor and/or a chemotherapeutic agent).

In one embodiment, the amount or dosage of the ACAT1 inhibitor, the antitumor agent, or both, used in combination, does not exceed the level at which each agent is used individually, e.g., as a monotherapy. In one embodiment, the amount or dosage of the ACAT1 inhibitor, the antitumor agent, or both, used in combination, is lower (e.g., at least 20%, at least 30%, at least 40%, or at least 50% lower) than the amount or dosage of each agent used individually, e.g., as a monotherapy. In one embodiment, the amount or dosage of the ACAT1 inhibitor, the antitumor agent, or both, used in combination that results in treatment of cancer is lower (e.g., at least 20%, at least 30%, at least 40%, or at least 50% lower) than the amount or dosage of each agent used individually, e.g., as a monotherapy.

In one embodiment, the ACAT1 inhibitor is administered intravenously, intramuscularly, parenterally, nasally or orally. In one embodiment, the antitumor agent is administered intravenously, intramuscularly, parenterally, nasally or orally. In one embodiment, the ACAT1 inhibitor is administered prior to, after, or concurrently with the antitumor agent.

Kits

Compositions (including, for example, formulations and unit dosages) comprising an ACAT1 inhibitor, as disclosed herein, can be prepared and placed in an appropriate container, and labeled for treatment of an indicated condition (e.g., cancer). Accordingly, provided is also an article of manufacture, such as a container comprising a unit dosage form of an ACAT1 inhibitor, as disclosed herein, and a label containing instructions for use of the compounds and compositions. In one embodiment, the article of manufacture is a container comprising a unit dosage form of an ACAT1 inhibitor, as disclosed herein, and a pharmaceutically acceptable carrier. In one embodiment, the unit dosage form for the ACAT1 inhibitor is a tablet or a capsule.

In one embodiment, compositions (including, for example, formulations and unit dosages) comprising an ACAT1 inhibitor, as disclosed herein, and compositions comprising an antitumor agent (e.g., an immune checkpoint inhibitor and/or a chemotherapeutic agent), as disclosed herein, can be prepared and placed in an appropriate container, and labeled for treatment of an indicated condition (e.g., cancer). Accordingly, provided is also an article of manufacture, such as a container comprising a unit dosage form of an ACAT1 inhibitor and a unit dosage form of an antitumor agent, as disclosed herein, and a label containing instructions for use of the compositions. In one embodiment, the article of manufacture is a container comprising (i) a unit dosage form of an ACAT1 inhibitor, as disclosed herein, and a pharmaceutically acceptable carrier; and (ii) a unit dosage form of an antitumor agent, as disclosed herein, and a pharmaceutically acceptable carrier. In one embodiment, the unit dosage form for both the ACAT1 inhibitor and the antitumor agent is a tablet or a capsule. In one embodiment, the unit dosage form for the ACAT1 inhibitor is a tablet or a capsule and the unit dosage form for the antitumor agent is solution.

Kits also are contemplated. For example, a kit can comprise unit dosage forms of an ACAT1 inhibitor, as disclosed herein, and a package insert containing instructions for use of the kit in treatment of a medical condition. In one embodiment, the kit comprises a unit dosage form of the ACAT1 inhibitor, as disclosed herein, and a pharmaceutically acceptable carrier. In one embodiment, the unit dosage form for the ACAT1 inhibitor is a tablet or capsule. In one embodiment, the kit can comprise unit dosage forms of an ACAT1 inhibitor, as disclosed herein, and unit dosage forms of an antitumor agent, as disclosed herein, and a package insert containing instructions for use of the kit in treatment of a medical condition. In one embodiment, the kit comprises (i) a unit dosage form of the ACAT1 inhibitor, as disclosed herein, and a pharmaceutically acceptable carrier; and (ii) a unit dosage form of an antitumor agent, as disclosed herein, and a pharmaceutically acceptable carrier. In one embodiment, the unit dosage form for both the ACAT1 inhibitor and the antitumor agent is a tablet or capsule. In one embodiment, the unit dosage form for the ACAT1 inhibitor is a tablet or capsule while the unit dosage form for the antitumor agent is a solution.

The instructions for use in the kit may be for treating a cancer, including, for example, melanoma or lung cancer, as further described herein.

Pharmaceutical Compositions and Modes of Administration

In one embodiment, this disclosure provides a composition comprising an ACAT1 inhibitor. In one embodiment, this disclosure provides a composition comprising an ACAT1 inhibitor and an antitumor agent. In one embodiment, the antitumor agent disclosed herein may be an immune checkpoint inhibitor (e.g., anti-PD-1) and/or a chemotherapeutic agent (e.g., dacarbazine).

In one embodiment, this disclosure provides a co-formulation comprising an ACAT1 inhibitor, an antitumor agent, and a pharmaceutically acceptable carrier. In one embodiment, this disclosure provides a co-formulation comprising a therapeutically effective amount of an ACAT1 inhibitor, a therapeutically effective amount of an antitumor agent, and a pharmaceutically acceptable carrier.

Any effective regimen for administering the pharmaceutical compositions and/or co-formulations can be used. For example, the pharmaceutical compositions and/or co-formulations may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. The route of administration may also depend on the type of cancer. For example, for cancers such as lymphoma or leukemia, the administration may be systemic, whereas a localized delivery may be used for treating a tumor. Further, a staggered regimen, for example, one to five days per week can be used as an alternative to daily treatment.

In one embodiment, separate or sequential administration of the ACAT1 inhibitor and antitumor agent(s) is necessary to facilitate delivery of the composition into the patient. In one embodiment, the ACAT1 inhibitor and antitumor agent(s) can be administered at different dosing frequencies or intervals. For example, the ACAT1 inhibitor can be administered daily, while the antitumor agent(s) can be administered less frequently. Additionally, as will be apparent to those skilled in the art, the ACAT1 inhibitor and antitumor agent(s) can be administered using the same route of administration or different routes of administration. In one embodiment, the immune checkpoint inhibitors (e.g., antibodies or fragments thereof targeting immune checkpoint proteins) are administered intravenously or by intra-arterial injection. In one embodiment, the chemotherapeutic agents (e.g., dacarbazine) are administered intravenously or by intra-arterial injection. In one embodiment, the small molecule drugs are administered orally or parenterally. In one embodiment, the ACAT1 inhibitor is administered orally and the antitumor agent(s) is administered parenterally. In one embodiment, the ACAT1 inhibitor and antitumor agent(s) are administered parenterally. In one embodiment, the ACAT1 inhibitor and antitumor agent(s) are administered orally. In one embodiment, the ACAT1 inhibitor is administered prior to, after, or concurrently with the antitumor agent(s).

In one embodiment, the ACAT1 inhibitors and/or antitumor agent(s) described herein may be administered orally. Oral administration may be via, for example, capsule or enteric coated tablets. In making the pharmaceutical compositions that include at least an ACAT1 inhibitor, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active agents, soft and hard gelatin capsules, sterile injectable solutions, and sterile packaged powders.

For preparing solid compositions such as tablets, the principal active ingredient may be mixed with a pharmaceutical carrier or excipient to form a solid preformulation composition containing a homogeneous mixture of an ACAT1 inhibitor and/or an antitumor agent. When referring to these preformulation compositions as homogeneous, the active ingredient may be dispersed evenly throughout the composition so that the composition may be readily subdivided into equally effective unit dosage forms such as tablets, pills and capsules. In one embodiment, the tablets or pills disclosed herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Some examples of suitable carriers or excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employs transdermal delivery devices ("patches"). Such transdermal patches may be used to provide continuous or discontinuous infusion of the compounds and compositions disclosed herein in controlled amounts. The construction and use of transdermal patches for the delivery of pharmaceutical agents is well known in the art. Such patches may be constructed for continuous, pulsatile, or on demand delivery of pharmaceutical agents.

In one embodiment, the compositions provided are formulated as a solution for delivery into a patient for treating cancer. Diluent or carriers employed in the compositions can be selected so that they do not diminish the desired effects of the ACAT1 inhibitor and/or antitumor agents. Examples of suitable compositions include aqueous solutions, for example, a solution in isotonic saline, 5% glucose. Other well-known pharmaceutically acceptable liquid carriers such as alcohols, glycols, esters and amides, may be employed. In one embodiment, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In one embodiment, the compositions disclosed herein can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly (glycolic acid), copolymers of lactic and glycolic acids, or other polymeric agents both natural and synthetic.

Dosing

The dosing regimen of an ACAT1 inhibitor (e.g., avasimibe) in the methods provided herein may vary depending upon the indication, route of administration, and severity of the condition. For instance, depending on the route of administration, a suitable dose can be calculated according to body weight, body surface area, or organ size. The final dosing regimen is determined by the attending physician in view of good medical practice, considering various factors that modify the action of drugs, e.g., the specific activity of the agent/compound, the identity and severity of the disease state, the responsiveness of the subject, the age, condition, body weight, sex, and diet of the subject, and the severity of any infection. Additional factors that can be taken into account include time and frequency of administration, drug combinations, reaction sensitivities, and tolerance/response to therapy. Further refinement of the doses appropriate for treatment involving any of the formulations mentioned herein is done routinely by the skilled practitioner without undue experimentation, especially in light of the dosing information and assays disclosed, as well as the pharmacokinetic data observed in human clinical trials. Appropriate doses can be ascertained through use of established assays for determining concentration of the agent in a body fluid or other sample together with dose response data.

As indicated above, the dose and frequency of dosing may depend on pharmacokinetic and pharmacodynamic, as well as toxicity and therapeutic efficiency data. For example, pharmacokinetic and pharmacodynamic information about the ACAT1 inhibitor can be collected through preclinical in vitro and in vivo studies, later confirmed in humans during the course of clinical trials. Thus, for the ACAT1 inhibitors disclosed herein, a therapeutically effective dose can be estimated initially from biochemical and/or cell-based assays. The dosage can then be formulated in animal models to achieve a desirable circulating concentration range that inhibits ACAT1 activity or expression. As human studies are conducted, further information will emerge regarding the appropriate dosage levels and duration of treatment for various diseases and conditions.

Toxicity and therapeutic efficacy of an ACAT1 inhibitor and/or an antitumor agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds and compositions that exhibit large therapeutic indices, i.e., the toxic dose is substantially higher than the effective dose, are preferred. The data obtained from such cell culture assays and additional animal studies can be used in formulating a range of dosage for human use. The doses of such compounds and compositions lies preferably within a range of circulating concentrations that include the $ED_{50}$ with little or no toxicity.

In one embodiment, a therapeutically effective amount of an ACAT1 inhibitor is an amount sufficient to inhibit ACAT1 expression and/or activity, and thereby treat a human suffering an indication (e.g., cancer), or to ameliorate or alleviate the existing symptoms of the indication. The dose administered of any of the compositions disclosed herein may be administered once daily (QD), twice daily (BID), three times daily, four times daily, or more than four times daily using any suitable mode described herein.

Moreover, administration or treatment with the compositions disclosed herein may be continued for a number of days; for example, treatment may continue for at least 7 days, 14 days, or 28 days, for one cycle of treatment. Treatment cycles are well known, and are frequently alternated with resting periods of about 1 to 28 days, commonly about 7 days or about 14 days, between cycles. The treatment cycles, in other embodiments, may also be continuous.

In one embodiment, In one embodiment, an ACAT1 inhibitor is administered to a human at a dose between 10 mg and 1200 mg, between 20 mg and 1200 mg, between 20 mg and 1000 mg, between 20 mg and 800 mg, between 20 mg and 500 mg, between 50 mg and 500 mg, between 100 mg and 400 mg, between 100 mg and 300 mg, or between 100 mg and 200 mg. In one embodiment, the therapeutically effective amount of the ACAT1 inhibitor is administered to a human at a dose of about 10 mg, about 20 mg, about 40 mg, about 50 mg, about 75 mg, about 100 mg, about 200 mg, about 300 mg, about 400 mg, about 500 mg, about 600 mg, about 700 mg, about 800 mg, about 1,000 mg, or about 1,200 mg. It will be understood, however, that the amount of the compound and compositions actually administered usually will be determined by a physician, in the light of the relevant circumstances, including the condition to be treated, the chosen route of administration, the actual compound/composition administered and its relative activity, the age, weight, and response of the individual subject, and the severity of the subject's symptoms.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

Example 1. Methods for Testing ACAT1 Inhibitor Monotherapy and Combined Therapy

This example provides materials and methods for evaluating the activity of an ACAT1 inhibitor (e.g., avasimibe) and the combination of ACAT1 inhibitor and an antitumor agent (e.g., anti-PD-1 inhibitor or dacarbazine) as shown in Examples 2-5.

Reagents and Mice

DMEM and FBS was from Life Technologies. Filipin, Lovastatin, MβCD-cholesterol, and MβCD were from Sigma. Amplex Red cholesterol assay kit was from Invitrogen. IL-2 was from Promega. For the flow cytometric analysis, α-mCD4 (RM4-5), α-mCD8 (53-6.7), α-mCD3ε (145-2C11), α-IFN-γ (XMG1.2), α-TNF-α (MP6-XT22), α-Granzyme B (NGZB), α-CD44 (IM7), α-CD69 (H1.2F3) PD-1 (J43), CTLA-4 (UC10-4B9), Ki67 (16A8), Foxp3 (FJK-16s), Gr1 (RB6-8C5), CD11b (M1/70) and CD45 (30-F11) were purchased from eBioscience. For western blots, α-pCD3ζ, α-CD3ζ, α-pZAP70, α-ZAP70, α-pLAT, α-LAT, α-pErk1/2, α-Erk1/2 were purchased from Cell Signaling Technology. Avasimibe was from Selleck. U18666A was from Merck. K604 was chemically synthesized in Fa-Jun Nan's laboratory, Shanghai Institute of Materia Medica, Chinese Academy of Sciences. CP113, 818 was a research gift from Pierre Fabre. MTS (3-(4,5-dimethylthiazol-2-yl)-5-(3-carboxymethoxyphenyl)-2-(4-sulfophenyl)-2H-tetrazolium) was from Promega. B16F10, Lewis lung carcinoma (LLC) and EL-4 cell lines were originally obtained from the American Type Culture Collection, and proved mycoplasma-free. *Listeria monocytogenes* was generously provided by Dr. Qibing Leng, Institute Pasteur of Shanghai, Chinese Academy of Sciences.

C57BL/6 mice were purchased from SLAC (Shanghai, China). OT-I TCR transgenic mice were from the Jackson Laboratory. CD4$^{Cre}$ transgenic mice was obtained. InGeneious Labs (Stony Brook, N.Y., USA) produced homozygous Acat1$^{flox/flox}$ mouse. To produce this mouse, the Acat1LoxP construct was made by inserting two LoxP sites covering Acat1 exon 14, which includes His460 known to be essential for the enzymatic activity. The construct was injected into ES cells. The correctly-targeted clones as determined by Southern blot and diagnostic PCR were injected into C57BL/6 blastocysts. In order to remove Neo marker, the mice were further backcrossed to the C57BL/6 Frt mice. Through mouse crossing, the WT Acat1 allele (Acat1$^{+/+}$), heterozygous Acat1 LoxP allele (Acat1$^{flox/+}$) and homozygous Acat1 LoxP allele (Acat1$^{flox/flox}$) were obtained and confirmed by using diagnostic PCR. Acat1$^{flox/flox}$ mice were crossed with CD4$^{cre}$ transgenic mice to get Acat1$^{CKO}$ mice with ACAT1 deficiency in T cells. Acat1$^{CKO}$ mice were further crossed with OT-I TCR transgenic mice to get Acat1$^{CKO}$-OT-I mice. Animal experiments using Acat1$^{CKO}$ mice were controlled by their littermates with normal ACAT1 expression (Acat1$^{flox/flox}$). Animal experiments using Acat1$^{CKO}$-OT-I mice were controlled by their littermate with normal ACAT1 and OT-I TCR expression (Acat1$^{flox/flox}$-OT-I). Acat2$^{-/-}$ mice were purchased from Jackson Laboratory. All mice were maintained in pathogen-free facilities at the Shanghai Laboratory Animal Center. All animal experiments used mice with matched age and sex. Animals were randomly allocated to experimental groups. The animal experiments performed with a blinded manner were described below. All animal experiments were approved by The Institutional Animal Use Committee of the Institute of Biochemistry and Cell Biology, Shanghai Institutes for Biological Sciences, Chinese Academy of Sciences. All human studies have been approved by the Research Ethical Committee from ChangZheng Hospital, Shanghai, China. Informed consent was obtained from all study subjects.

Quantitative Reverse Trancriptase-PCR

Total RNA was extracted with Trizol (Life technology) from the indicated cells and subjected to qRT-PCR using gene specific primers (5'-3'): Acat1 (Forward, GAAACCGGCTGTCAAAATCTGG (SEQ ID NO: 1); Reverse, TGTGACCATTTCTGTATGTGTCC (SEQ ID NO: 2)); Acat2 (Forward, ACAAGACAGACCTCTTCCCTC (SEQ ID NO: 3); Reverse, ATGGTTCGGAAATGTTCACC (SEQ ID NO: 4)); Nceh (Forward, TTGAATACAGGCTAGTCCCACA (SEQ ID NO: 5); Reverse, CAACGTAGGTAAACTGTTGTCCC (SEQ ID NO: 6)); Srebp1 (Forward, GCAGCCACCATCTAGCCTG (SEQ ID NO: 7); Reverse, CAGCAGTGAGTCTGCCTTGAT (SEQ ID NO: 8)); Srebp2 (Forward, GCAGCAACGGGACCATTCT (SEQ ID NO: 9); Reverse, CCCCATGACTAAGTCCTTCAACT (SEQ ID NO: 10)); Acaca (Forward, ATGGGCGGAATGGTCTCTTTC (SEQ ID NO: 11); Reverse, TGGGGACCTTGTCTTCATCAT (SEQ ID NO: 12)); Fasn (Forward, GGAGGTGGTGATAGCCGGTAT (SEQ ID NO: 13); Reverse, TGGGTAATCCATAGAGCCCAG (SEQ ID NO: 14)); Hmgcs (Forward, AACTGGTGCAGAAATCTCTAGC (SEQ ID NO: 15); Reverse, GGTTGAATAGCTCAGAACTAGCC (SEQ ID NO: 16)); Hmgcr (Forward, AGCTTGCCCGAATTGTATGTG (SEQ ID NO: 17); Reverse, TCTGTTGTGAACCATGTGACTTC (SEQ ID NO: 18)); Sqle (Forward, ATAAGAAATGCGGGGATGTCAC (SEQ ID NO: 19); Reverse, ATATCCGAGAAGGCAGCGAAC (SEQ ID NO: 20)); Ldlr (Forward, TGACTCAGACGAACAAGGCTG (SEQ ID NO: 21), Reverse, ATCTAGGCAATCTCGGTCTCC (SEQ ID NO: 22)); Idol (Forward, TGCAGGCGTCTAGGGATCAT (SEQ ID NO: 23); Reverse, GTTTAAGGCGGTAAGGTGCCA (SEQ ID NO: 24)); Abca1 (Forward, AAAACCGCAGACATCCTTCAG (SEQ ID NO: 25); Reverse, CATACCGAAACTCGTTCACCC (SEQ ID NO: 26)); Abcg1 (Forward, CTTTCCTACTCTGTACCCGAGG (SEQ ID NO: 27); Reverse, CGGGGCATTCCATTGATAAGG (SEQ ID NO: 28)); Ifng (Forward, ATGAACGCTACACACTGCATC (SEQ ID NO: 29); Reverse, CCATCCTTTTGCCAGTTCCTC (SEQ ID NO: 30)).

Measurement of the Cholesterol Level of T Cells

Three methods were used to measure the cholesterol level of T cells as shown below.

Filipin staining: Filipin III was dissolved in ethanol to reach the final concentration of 5 mg/ml. Cells were fixed with 4% PFA and stained with 50 μg/ml filipin III for 30 minutes at 4° C. Images were collected using a Leica SP8 confocal microscope and analyzed using a Leica LAS AF software.

PM cholesterol oxidation-based assay: The total cellular cholesterol was quantified using the Amplex Red cholesterol assay kit (Invitrogen). To quantify the intracellular cholesterol, CD8+ T cells were fixed with 0.1% glutaraldehyde and then treated with 2 U/ml cholesterol oxidase for 15 minutes to oxidise the plasma membrane cholesterol. The intracellular cholesterol was then extracted with methanol/chloroform (vol/vol, 1:2), and quantified using the Amplex Red cholesterol assay kit. The value of the plasma membrane cholesterol was obtained by subtracting the intracellular cholesterol from the total cellular cholesterol.

Biotinylation-based PM lipid purification and quantitation: The plasma membrane of CD8+ T cells was biotinylated by 1 mg/ml sulfo-NHS-S-Biotin, and then the cells were lysed by passing 13 times through a ball-bearing homogenizer. Plasma membrane was isolated from the supernatant of homogenate by streptavidin magnetic beads. Lipids were extracted with hexane/isopropanol (vol/vol, 3:2), and then were used for measurement of unesterified cholesterol with Amplex Red Cholesterol Assay Kit and choline-containing phospholipids with EnzyChrom Phospholipid Assay Kit. The relative cholesterol level was normalized by the total phospholipids.

Modulation of the Plasma Membrane Cholesterol Level by MβCD and MβCD-Coated Cholesterol To deplete cholesterol from the plasma membrane, CD8+ T cells were treated with 0.1-1 mM MβCD for 5 minutes at 37° C., and then washed three times with PBS. To add cholesterol to the plasma membrane, CD8+ T cells were incubated with the culture medium supplied with 1-20 μg/ml MβCD-coated cholesterol at 37° C. for 15 minutes. The cells were then washed three times with PBS.

T Cell Isolation and Effector Function Analysis

Peripheral T cells were isolated from mouse spleen and draining lymph nodes by a CD8+ or CD4+ T cell negative selection kit (Stem cell). To analyse the tumour-infiltrating T cells, tumours were first digested by collagenase IV (sigma), and tumour-infiltrating leukocytes were isolated by 40-70% percoll (GE) gradient centrifugation. To measure the effector function of CD8+ T cells, the isolated cells were first stimulated with 1 μM ionomycin and 50 ng/ml PMA for 4 hours in the presence of 5 μg/ml BFA, and then stained with PERCP-α-CD8a. Next, cells were fixed with 4% PFA and stained with FITC-α-Granzyme B, APC-α-IFNγ and PE-α-TNFα. In general, to gate the cytokine or granule producing cells, T cells without stimulation or stained with isotype control antibody were used as negative controls. This gating strategy is applicable for most of the flow cytometric analyses. To detect the MDSCs (myeloid-derived suppressor cells) in the tumour, the percoll isolated leukocyte were stained with α-CD45, α-CD11b and α-Ly6G (Gr1), the CD45+ population was gated, after which the MDSC population (CD11b+ Gr1+) in CD45+ were gated.

Antigen Stimulation of CD8+ T cells

A pan T cell isolation kit (Miltenyi biotech) was used to deplete T cells from splenocytes isolated from C57BL/6 mice. The T cell-depleted splenocytes were pulsed with antigenic peptides for 2 hours and washed three times. SIINFEKL (OVA$_{257-264}$ or N4), SAINFEKL (A2), SIITFEKL (T4), SIIGFEKL (G4) are four types of agonist antigens with strong to weak TCR affinities. RTYTYEKL (Catnb) is a self-antigen of OT-I TCR. SIIRFEKL (R4) supports the positive selection of OT-I T cells and thus mimics a self-antigen. The T cell-depleted and antigen-pulsed splenocytes were co-incubated with Acat1$^{CKO}$-OT-I T cells or WT OT-I T cells for 24 hours. Cytokine production of CD8+ T cells was measured by intracellular staining and flow cytometric analysis.

Measurement of CD8+ T-cell Cytotoxicity

To generate mature Cytotoxic T lymphocytes (CTLs), splenocytes isolated from Acat1$^{CKO}$-OT-I mice or WT OT-I mice were stimulated with OVA$_{257-264}$ (N4) for 3 days in the presence of 10 ng/ml IL-2. Cells were centrifuged and cultured in fresh medium containing 10 ng/ml IL-2 for 2 more days, after which most of the cells in the culture were CTLs. To measure CD8+ T-cell cytotoxicity, EL-4 cells were pulsed with 2 nM antigenic peptide (N4, A2, T4, G4, R4 or Catnb) for 30 minutes. After washing EL-4 cells and CTLs three times with PBS, we mixed CTLs and antigen-pulsed EL-4 cells (1×10$^5$) in the killing medium (phenol free-RPMI 1640, 2% FBS), at the ratio of 1:1, 1:2 and 1:5, respectively. After 4 hours, the cytotoxic efficiency was measured by quantifying the release of endogenous lactate dehydrogenase (LDH) from EL-4 cells using a CytoTox 96 Non-Radioactive Cytotoxicity kit (Promega).

Measurement of Human CD8+ T-Cell Cytokine Production

Human peripheral blood mononuclear cells (PBMCs) from healthy donors were stimulated with 5 μg/ml PHA (Sigma) for 2 days and then rested for 1 day. Cells were pretreated with vehicle (DMSO), CP113, 818 or avasimibe for 12 hours and then stimulated with plate-bound α-CD3 (5 μg/ml) and α-CD28 (5 μg/ml) antibodies for 24 hours. Intracellular staining and flow cytometry were used to assess cytokines production of CD8+ T cells.

T Cell Metabolism

Oxygen consumption rates (OCR) and extracellular acidification rates (ECAR) were measured in nonbuffered DMEM (sigma) containing either 25 mM or 10 mM glucose, 2 mM L-glutamine, and 1 mM sodium pyruvate, under basal conditions and in response to 1 μM oligomycin (to block ATP synthesis), 1.5 μM FCCP (to uncouple ATP synthesis from the electron transport chain, ETC), 0.5 μM rotenone and antimycin A (to block complex I and III of the ETC, respectively), and 200 μM etomoxir (to block mitochondrial FAO) on the XF-24 or XF-96 Extracellular Flux Analyzers (Seahorse Bioscience) according to the manufacturer's recommendations.

Measurement of Cell Viability with MTS Assay

B16F10 cells (5×10$^3$) in 100 μl media containing avasimibe or DMSO were cultured for 24, 48 or 72 hours. 20 μl of MTS reagent (CellTiter 96® AQueous One Solution Cell Proliferation Assay, Promega) was added into each well. After 2-3 hour incubation, the absorbance at 490 nm was measured. The effect of avasimibe on cell viability was obtained by normalizing the absorbance of avasimibe-treated cells with that of the DMSO-treated cells. The viability value of DMSO-treated cells was set as 1.

*Listeria monocytogenes* Infection

*L. monocytogenes* (2-7×10$^4$ CFU) expressing a truncated OVA protein were intravenously injected into Acat1$^{CKO}$ and littermate WT mice at age of 8-10 weeks. On Day 6, T cells isolated from spleens were stimulated with 50 ng/ml PMA and 1 μM lonomycin for 4 hours in the presence of Brefeldin A and then assessed by flow cytometry to detect IFNγ production. At the same time, the serum IFNγ level was assessed by ELISA. To detect the antigen specific response of CD8+ T cells, the splenocytes were stimulated with 1 μM OVA257-264 peptide for 24 hours. IFNγ production was analyzed as mentioned above. To detect the *L. monocytogenes* titer in the livers of infected mice, the livers were homogenized in 10 ml 0.2% (vol/vol) Nonidet P-40 in PBS, and the organ homogenates were diluted and plated on agar plates to determine the CFU of L. monocytogenes. Investigator was blinded to group allocation during the experiment and when assessing the outcome.

Melanoma Mouse Models

B16F10 cells were washed three times with PBS, filtered by a 40 μm strainer. In a skin melanoma model, B16F10 cells ($2\times10^5$) were subcutaneously injected into the dorsal part of mice (age of 8-10 weeks). From Day 10, tumour size was measured every 2 days, and animal survival rate was recorded every day. Tumour size was calculated as length× width. Mice with tumour size larger than 20 mm at the longest axis were euthanized for ethical consideration. To analyse effector function of tumour-infiltrating T cells, mice were euthanized on Day 16. In the avasimibe therapy, on Day 10 mice bearing tumour of similar size were randomly divided into two groups. From Day 10, avasimibe was injected intraperitoneally to the mice at the dose of 15 mg/kg every 2 days.

In a lung-metastatic melanoma model, B16F10 cells ($2\times10^5$) were intravenously injected into mice (age of 8-10 weeks). Animal survival rate was recorded every day. One Day 20, mice were euthanized and tumour number on lungs was counted. Next, lung-infiltrating T cells were isolated and analyzed as mentioned above. In the lung-metastatic melanoma model, investigator was blinded to group allocation during the experiment and when assessing the outcome.

T Cell Homing

B16F10-OVA cells ($2\times10^5$) were injected subcutaneously into C57BL/6 mice at the age of 8-10 weeks. On day 16, the naïve WT or $Acat1^{CKO}$ OT-I $CD8^+$ T cells were isolated and labeled with live cell dye CFSE or CTDR (Cell Tracker Deep Red, Life technologies), respectively. The labeled WT and CKO cells were mixed together at 1:1 ratio and $1\times10^7$ mixed cells per mouse were injected intravenously into the B16F10-OVA bearing mice. After 12 hours, blood, spleens, inguinal lymph nodes (draining) and mesenteric lymph nodes (non-draining) of the mice were collected. Single cell suspensions from these tissues were stained with the α-CD8a antibody, and the ratio of transferred cells in $CD8^+$ populations was analyzed using flow cytometry.

Lewis Lung Carcinoma (LLC) Model

The LLC cells were washed twice with PBS and filtered by a 40 μm strainer. After which, the LLC cells ($2\times10^6$) were intravenously injected into WT or $Acat1^{CKO}$ mice at the age of 8-10 weeks. To detect the tumour multiplicity in the lung, the mice were euthanized at Day 35 post tumour inoculation and tumour numbers in the lung were counted. In the avasimibe therapy, on Day 10 mice were randomly divided into two groups. From Day 10 to Day 35 post tumour inoculation, avasimibe was injected intraperitoneally to the mice at the dose of 15 mg/kg every 3 days.

Treatment of Melanoma by Adoptive T Cell Transfer

B16F10-OVA cells ($2\times10^5$) were injected subcutaneously into C57BL/6 mice at the age of 8-10 weeks. On Day 10, melanoma-bearing mice with similar tumour size were randomly divided into three groups (n=9-10) and respectively received PBS, WT OT-I CTLs ($1.5\times10^6$) or $Acat1^{CKO}$ OT-I CTLs ($1.5\times10^6$) by intravenous injection. From Day 13, the tumour size was measured every 2 days, and the animal survival rate was recorded every day. Tumour size was calculated as length×width. Mice with tumour size larger than 20 mm at the longest axis were euthanized for ethical consideration.

Treatment of Melanoma with Avasimibe, α-PD-1 Antibody or Avasimibe+α-PD-1 Antibody B16F10 cells ($2\times10^5$) were injected subcutaneously into C57BL/6 mice at age of 8-12 weeks. On Day 10, melanoma-bearing mice with similar tumour size were randomly divided into four groups (n=8-10) and received PBS, avasimibe, α-PD-1 antibody or avasimibe+α-PD-1 antibody respectively. Avasimibe was delivered every 2 days at the dose of 15 mg/kg by intragastric administration. α-PD-1 antibody (RMP1-14, Bio X Cell, 200 μg/injection) was injected intraperitoneally every 3 days. The tumour size and survival were measured as mentioned above.

Treatment of Melanoma with Avasimibe, Dacarbazine, or Avasimibe+Dacarbazine

B16F10 cells ($2\times10^5$) were injected subcutaneously into C57BL/6 mice at age of 8-12 weeks. On Day 10, melanoma-bearing mice with similar tumour size were randomly divided into four groups (n=9-13) and received PBS, avasimibe, dacarbazine, or avasimibe+dacarbazine respectively. Avasimibe was delivered every 2 days at the dose of 15 mg/kg by intragastric administration. Dacarbazine was injected intraperitoneally at the dose of 5 mg/kg. The tumour size and survival were measured as mentioned above.

Super-Resolution Stochastic Optical Reconstruction Microscopy (STORM) Imaging and Data Analysis Super-resolution STORM imaging was performed on a custom modified Nikon N-STORM microscope equipped with a motorized inverted microscope ECLIPSE Ti-E, an Apochromat TIRF 100× oil immersion lens with a numerical aperture of 1.49 (Nikon), an electron multiplying charge-coupled device (EMCCD) camera (iXon3 DU-897E, Andor Technology), a quad band filter composed of a quad line beam splitter (zt405/488/561/640rpc TIRF, Chroma Technology Corporation) and a quad line emission filter (brightline HC 446, 523, 600, 677, Semrock, Inc.).

The TIRF angle was adjusted to oblique incidence excitation at the value of 3950-4000, allowing the capture of images at about 1 μm depth of samples. The focus was kept stable during acquisition using Nikon focus system. For the excitation of Alexa647, the 647 nm continuous wave visible fiber laser was used, and the 405 nm diode laser (CUBE 405-100C, Coherent Inc.) was used for switching back the fluorophores from dark to the fluorescent state. The integration time of the EMCCD camera was 90-95 frames per second. To image TCR distribution in the plasma membrane, naïve $CD8^+$ T cells or activated $CD8^+$ T cells (stimulated with 10 μg/ml α-CD3 for 10 minutes at 37° C.) were fixed with 4% PFA, followed by surface staining with 2 μg/ml Alexa 647-α-CD3 for 2 hours at 4° C. Cells were placed in Ibidi 35 mm μ-Dish and the imaging buffer contained 100 mM β-Mercaptoethanolamin (MEA) for a sufficient blinking of fluorophores.

Super-resolution images were reconstructed from a series of 20,000-25,000 frames using the N-STORM analysis module of NIS Elements AR (Laboratory imaging s.r.o.). Molecule distribution and cluster position were analyzed with MATLAB (MathWorks) based on Ripley's K function. L(r)-r represents the efficiency of molecule clustering, and r value represents cluster radius. The r value at the maximum L(r)-r value represents the cluster size with the highest probability.

Imaging of Immunological Synapse by Total Internal Reflection Fluorescence Microscopy (TIRFM)

Planar lipid bilayers (PLBs) containing biotinylated lipids were prepared to bind biotin-conjugated antigen by streptavidin. Biotinylated liposomes were prepared by sonicating 1,2-dioleoyl-sn-glycero-3-phosphocholine and 1,2-dioleoylsn-glycero-3-phosphoethanolamine-cap-biotin (25:1 molar ratio, Avanti Polar Lipids) in PBS at a total lipid concentration of 5 mM. PLBs were formed in Lab-Tek chambers (NalgeNunc) in which the cover glasses were replaced with nanostrip-washed coverslips. Coverslips were incubated with 0.1 mM biotinylated liposomes in PBS for 20 minutes. After washing with 10 ml PBS, PLBs were incubated with 20 nM streptavidin for 20 minutes, and excessive streptavidin was removed by washing with 10 ml PBS. Streptavidin-containing PLBs were incubated with 20 nM bionylatedα-mCD3ε (145-2C11) (Biolegend). Excessive antibody was removed by washing with PBS. Next, PLBs were treated with 5% FBS in PBS for 30 minutes at 37° C. and washed thoroughly for TIRFM of T cells. Adhesion ligands necessary for immunological synapse formation were provided by treating the bilayer with serum.

Freshly isolated mouse splenocytes were stained with Alexa 568-α-mTCRβ Fab and FITC-α-mCD8 and washed twice. α-mTCRβ antibody was labeled with Alexa568-NHS ester (Molecular probes) and digested to get Fab fragments with Pierce Fab Micro Preparation Kit (Thermo). Cells were then placed on α-mCD3ε-containing PLBs to crosslink TCR. Time-lapse TIRF images were acquired on a heated stage with a 3-second interval time at 37° C., 5% $CO_2$, using a Zeiss Axio Observer SD microscopy equipped with a TIRF port, Evolve 512 EMCCD camera and Zeiss Alpha Plan-Apochromat 100× oil lens. The acquisition was controlled by ZEN system 2012 software. An OPSL laser 488 nm and a DPSS laser 561 nm were used. Field of 512×512 pixels was used to capture 6-8 $CD8^+$ T cells per image. Results of synapse formation and TCR movements were the population averages of all $CD8^+$ T cells from 2-3 individual images. The movements of TCR microclusters were splitted into directed, confined and random movement using the method described. To sort the three movements, the MSD plot of each TCR microcluster was fitted with three functions as described. The ones with good fit (square of correlation coefficients ($R^2$)≥0.33) were selected for further classification. For a certain TCR microcluter, the movement is defined as random if SD<0.010. The distinction of directed and confined movement depends on which function fit better in the population of those SD≥0.010. Images were analyzed with Image Pro Plus software (Media Cybernetics), ImageJ (NIH) and MATLAB (MathWorks).

Polarised Secretion of Cytolytic Granules

In the granule polarization imaging, CTLs stained with Alexa568-α-mTCRβ Fab were placed on α-mCD3ε-containing PLBs for indicated time and fixed with 4% PFA. After the permeabilization, cells were stained with Alexa488-α-mCD107a (1D4B) antibody. Three-dimensional spinning-disc confocal microscopy was used to image the granules polarized at 0-2 μm distance from the synapse. The total granule volumes were quantified with Imaris software.

The degranulation level was measured. OT-I CTLs were mixed with $OVA_{257-264}$ pulsed EL4 cells at 1:1 ratio. The mixed cells were then cultured in the medium supplemented with 1 μg/ml Alexa 488-α-CD107a antibody and 2 μM Monensin for 1, 2 and 4 hours. After which, cells were washed with PBS and further stained with PE-Cy7-α-CD8a antibody. Flow cytometry was used for assessing the surface and internalized CD107a levels.

Statistical Analysis

All sample sizes are large enough to ensure proper statistical analysis. Statistical analyses were performed using GraphPad Prism (GraphPad Software, Inc.). Statistical significance was determined. The P values less than 0.05 were considered significant, the level of significance was indicated as * $P<0.05$,  $P<0.01$ and * $P<0.001$. ns meant no significant difference. All of the t-test analysis in the experiments are two-tailed unpaired t-test.

The practice of the present disclosure will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

Example 2. Potentiated Effector Function of CD8+ T Cells by ACAT1 Inhibitors

A potent ACAT1/ACAT2 inhibitor (CP-113,818) and a less potent but specific ACAT1 inhibitor (K604) were used in this study. $CD8^+$ T cells were pretreated with vehicle (dimethylsulfoxide, DMSO), CP-113,818 or K604. Then the cells were stimulated with 5 μg $ml^{-1}$ plate-bound anti-CD3/CD28, and cytokine and cytolytic granule production was studied. Cytotoxicity of OT-I CTLs pretreated with CP-113,818 or K604 or vehicle was also studied.

Inhibiting cholesterol esterification by CP-113,818 or K604 augmented cytolytic granule and cytokine productions (FIG. 1, panels a and b) as well as cytotoxicity of $CD8^+$ T cells (FIG. 1, panels c and d). The results showed that inhibiting the activity of ACAT1 can significantly potentiate the effector function of the $CD8^+$ T cells.

In contrast, inhibiting cholesterol biosynthesis (e.g., using Lovastatin) or cholesterol transport (e.g., using U18666A) significantly decreased granule and cytokine productions of $CD8^+$ T cells.

Example 3. ACAT1-Deficient CD8+ T Cells $Acat1^{flox/flox}$ mice were crossed with $CD4^{cre}$ mice to generate conditional knockout (CKO) mice, in which Acat1 was conditionally knocked out in T cells. The transcriptional level of Acat2 in T cells was not changed in the $Acat1^{CKO}$ mice. ACAT1 deficiency did not affect thymocyte development or peripheral T-cell homeostasis. The T cells were isolated from wild-type (WT) and $Acat1^{CKO}$ (CKO) mice and were stimulated as described above. $Acat1^{CKO}$ mice were crossed with OT-I TCR transgenic mice (mice named $Acat1^{CKO}$ OT-I). Cytokine/granule productions of antibody stimulated WT and CKO $CD8^+$ T cells were studied. A skin melanoma model and a lung metastasis melanoma model were used to study the activity of $Acat1^{CKO}$ $CD8^+$ T cells in controlling tumour progression and metastasis. To study the TCR clustering and synapses formation on the plasma membrane, Ripley's K-function analysis of TCR molecules was performed. The r (radius) value at the maximal L(r)-r value of Ripley's K-function curves was studied. Total internal reflection fluorescence microscopy (TIRFM) analysis was used to study immunological synapse of $CD8^+$ T cells on stimulatory planar lipid bilayer. Cytolytic granule polarization and degranulation of OT-I CTLs was also studied.

Figure 2:
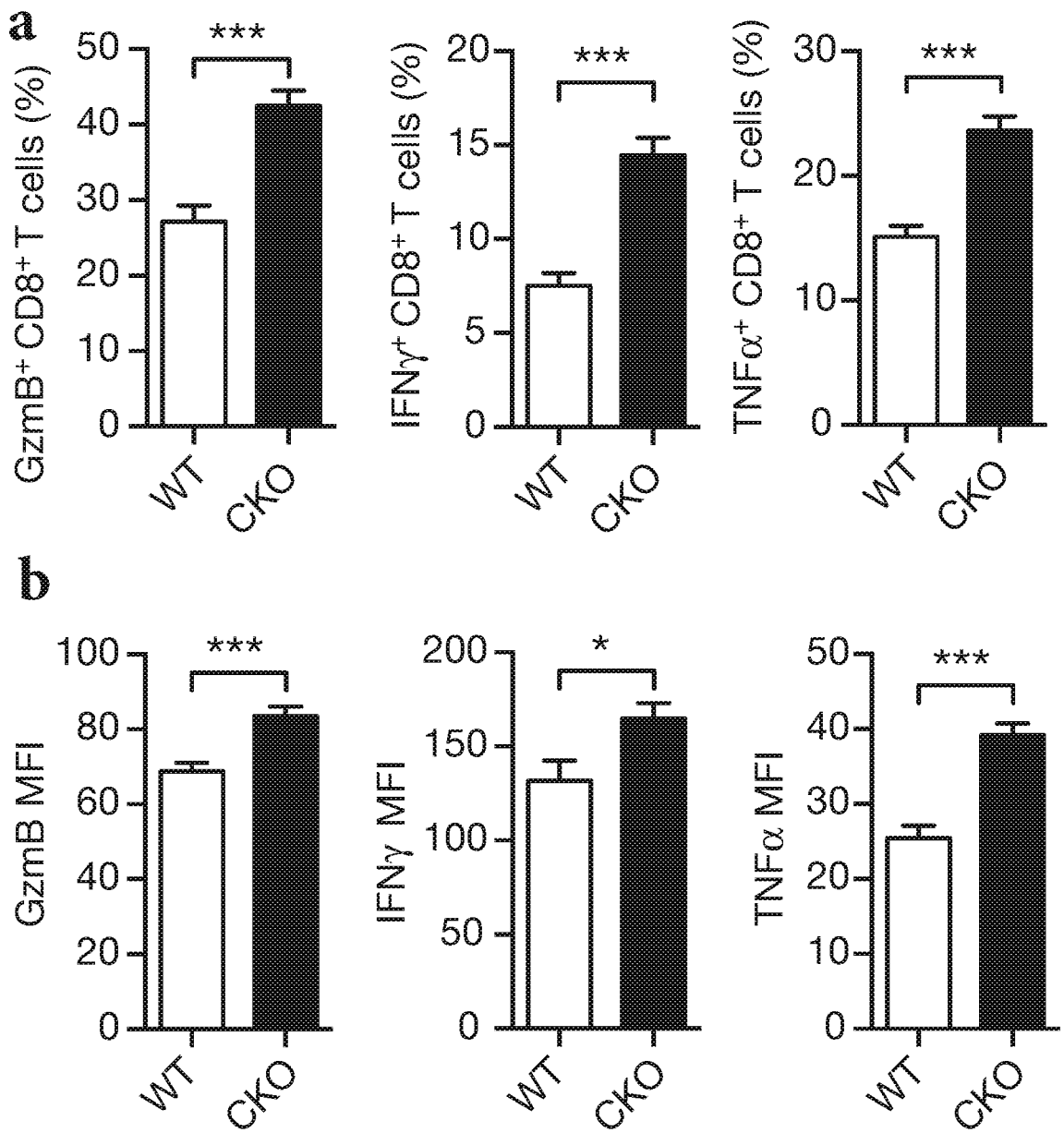
FIG. 2 shows enhanced cytokine/granule productions in ACAT1-deficient CD8+ T cells.
Figure 3:
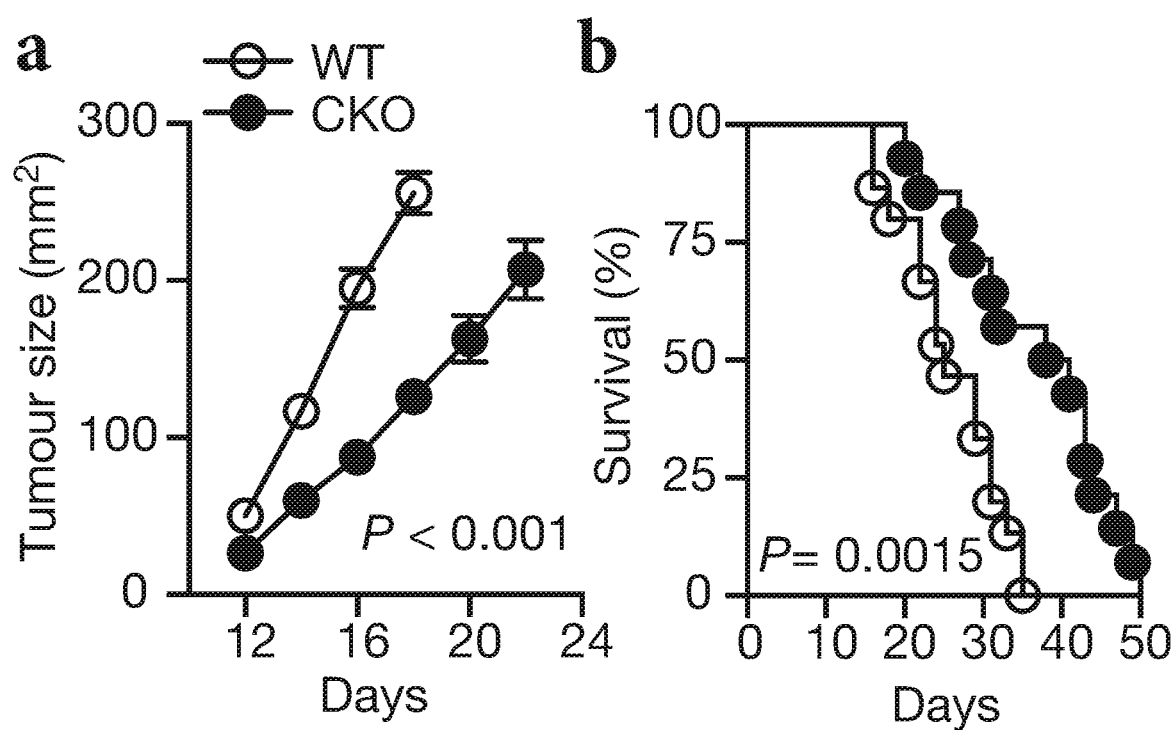
FIG. 3 shows inhibited tumor growth and prolonged survival time in ACAT1 conditional knockout (CKO) mice compared with wild type (WT) in a melanoma model.
Figure 4:
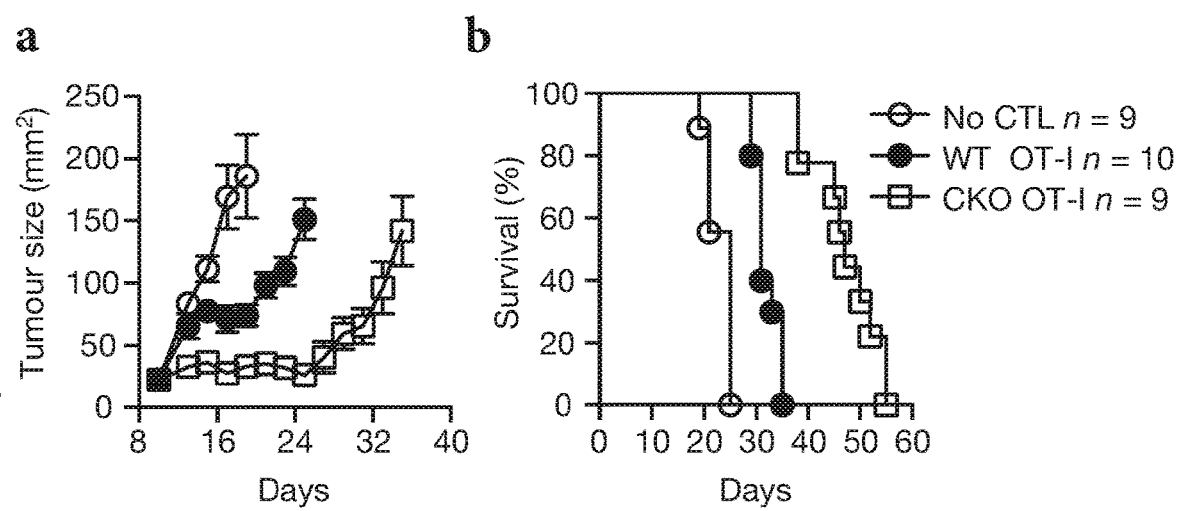
FIG. 4 shows stronger antitumor activity of transferred CKO OT-I cytotoxic T lymphocyte (CTLs) in melanoma mouse model.
Figure 5:
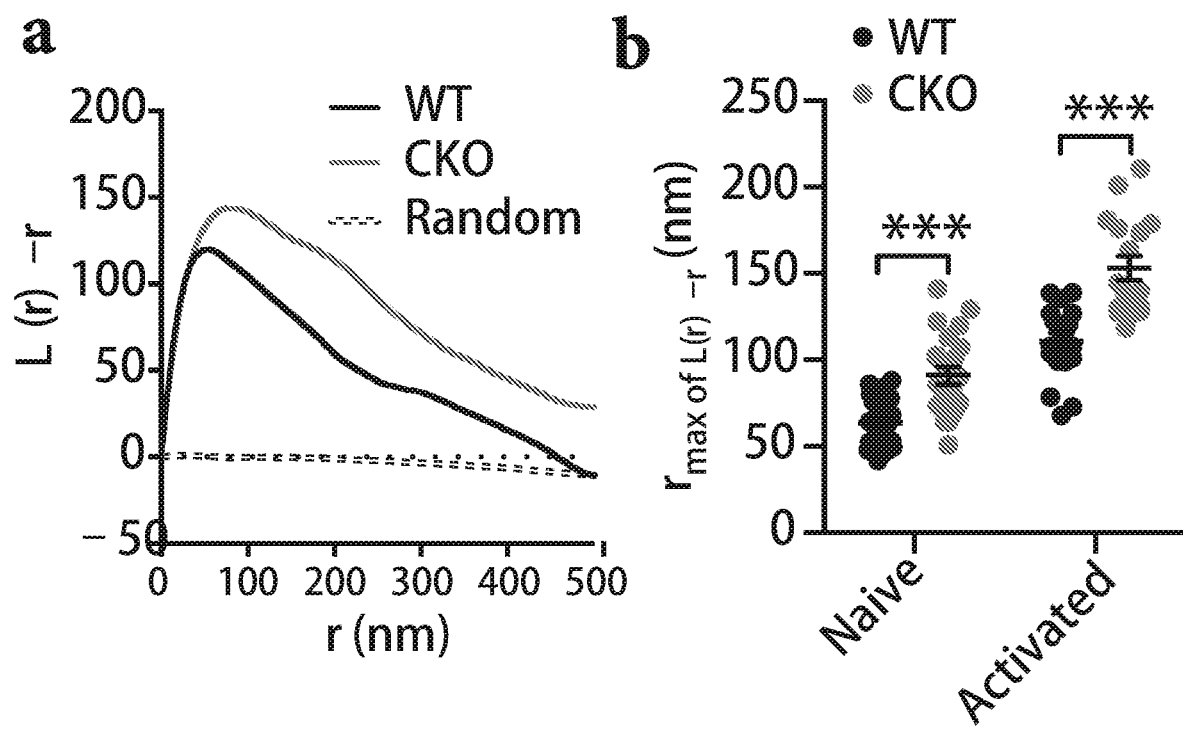
FIG. 5 shows enhanced T-cell receptor (TCR) clustering in ACAT1-deficient CD8+ T cells.
Figure 6:
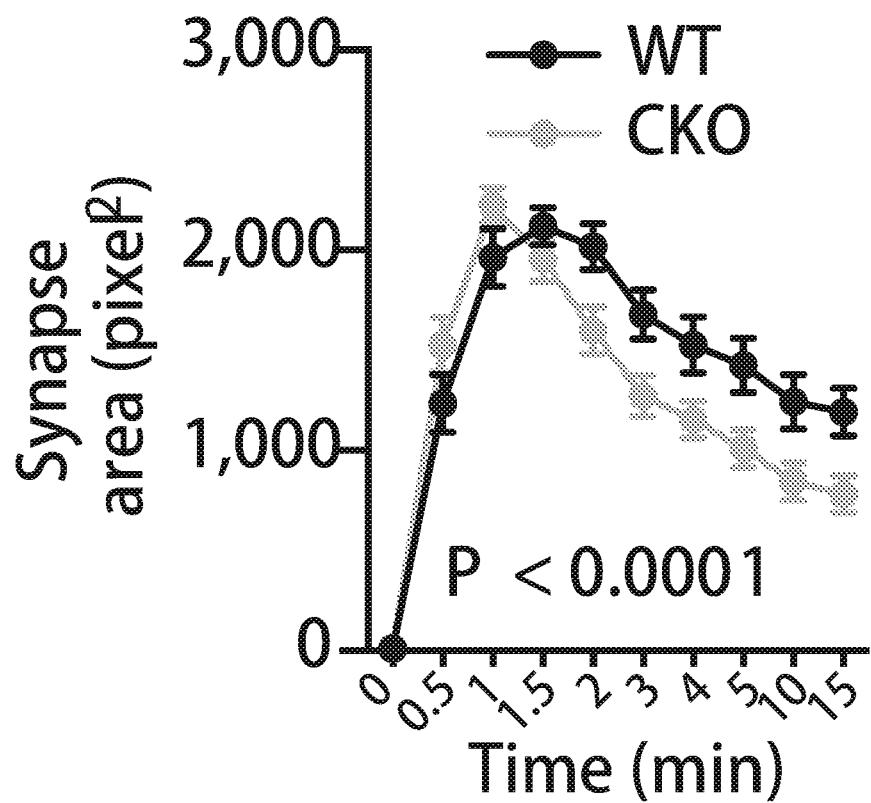
FIG. 6 shows augmented synapse formation on stimulatory planar lipid bilayer of ACAT1-deficient CD8+ T cells.
Figure 7:
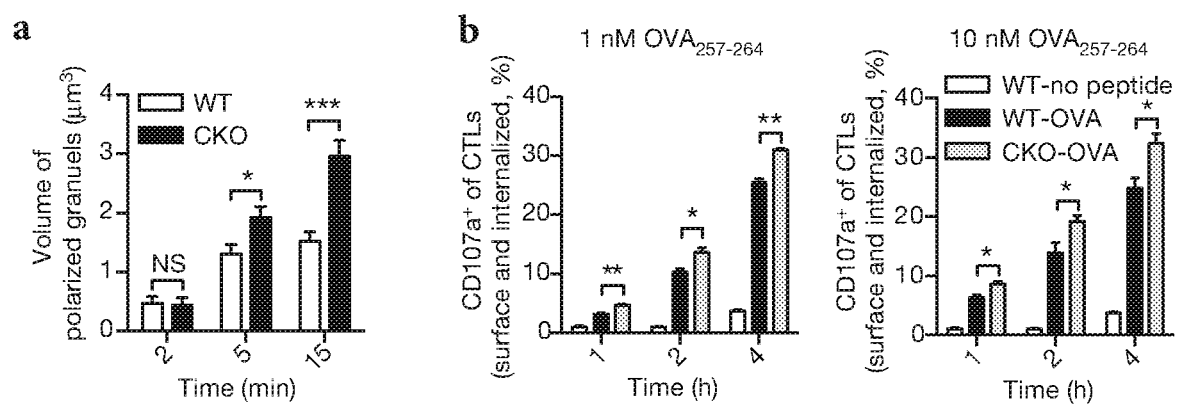
FIG. 7 shows augmented cytolytic granule polarization and degranulation in ACAT1-deficient CD8+ T cells.

Upon activation, the effector function of $Acat1^{CKO}$ $CD8^+$ T cells was significantly enhanced, as compared with WT $CD8^+$ T cells (FIG. 2, panels a and b). In the skin melanoma model, Acat1$^{CKO}$ mice had smaller tumour size (FIG. 3, panel a) and longer survival time (FIG. 3, panel b). Compared with WT, the transferred Acat1$^{CKO}$ OT-I Cytotoxic T lymphocytes (CTLs) showed stronger antitumor activity, evidenced by smaller tumour size (FIG. 4, panel a) and longer survival time (FIG. 4, panel b) of recipient mice. TCR microclusters of both naïve and activated Acat1$^{CKO}$ CD8$^+$ T cells were significantly larger than those of WT cells (FIG. 5, panels a and b). ACAT1 deficiency led to faster directed movement of TCR microclusters toward the centre of the synapse (FIG. 6, panels a and b). The mature immunological synapse of Acat1$^{CKO}$ CD8$^+$ T cells had more compact structure formed at a faster rate. The cytolytic granule polarization and the degranulation level were augmented in Acat1$^{CKO}$ CD8$^+$ T cells (FIG. 7).

Example 4. Combination of Avasimibe and Anti-PD-1

To study ACAT1 inhibitors in cancer immunotherapies in mice, melanoma-bearing mice were treated with a potent ACAT-1 inhibitor, avasimibe (Ava), or DMSO control, and tumour size and survival were studied. A combined therapy (avasimibe and anti-PD-1) or monotherapies (avasimibe or anti-PD-1) were also studied and compared in treating melanoma. In a lung cancer model, Lewis lung carcinoma-bearing mice were treated with avasimibe or DMSO control, and tumour multiplicity and survival were studied. Cytokine productions of stimulated human (h) CD8$^+$ T cells pretreated with avasimibe, CP-113,818, or DMSO. CTL cytotoxicity after avasimibe treatment was measured by the LDH assay. OT-I CTLs were pretreated with avasimibe or vehicle for 6 h and then incubated with EL-4 cells pulsed with OVA$_{257-264}$ peptide for 4 h.

Figure 8:
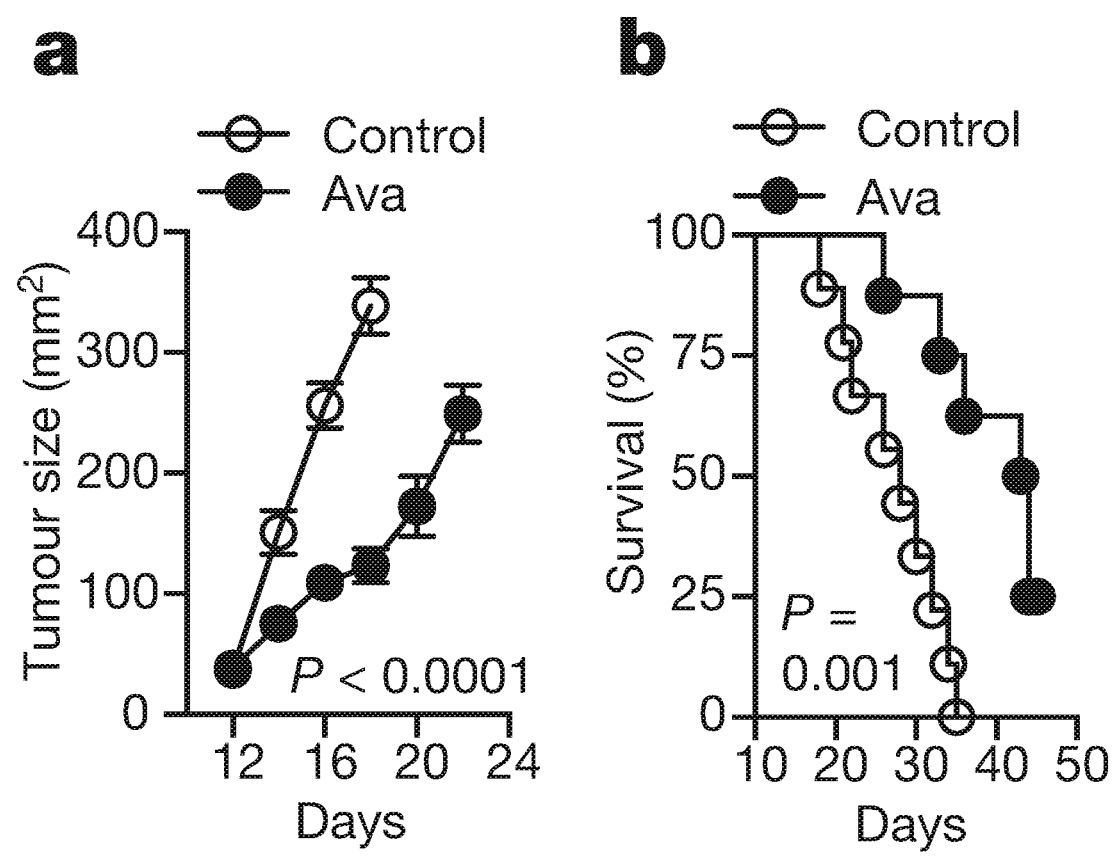
FIG. 8 shows inhibited tumor growth and prolonged survival time in melanoma bearing mice treated with an ACAT1 inhibitor, avasimibe.
Figure 9:
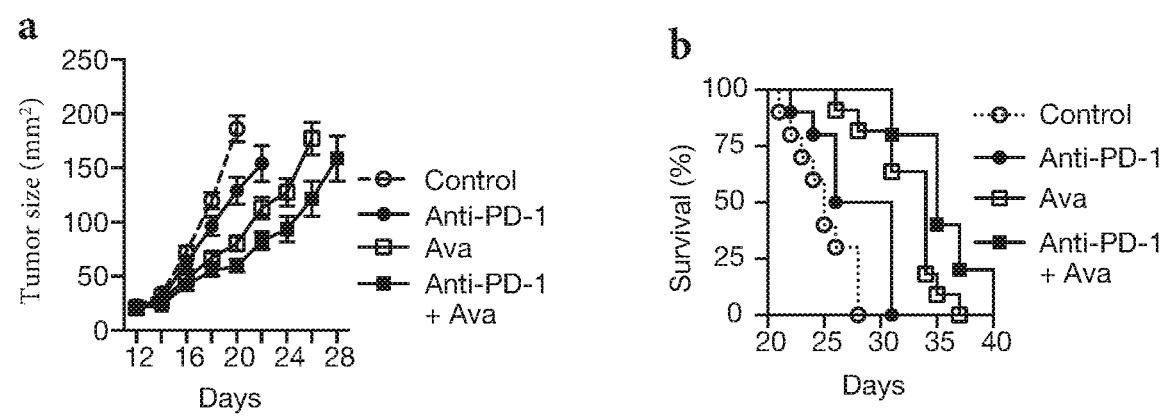
FIG. 9 shows a better antitumor efficacy of a combined therapy of avasimibe and anti-PD-1 than monotherapies.
Figure 10:
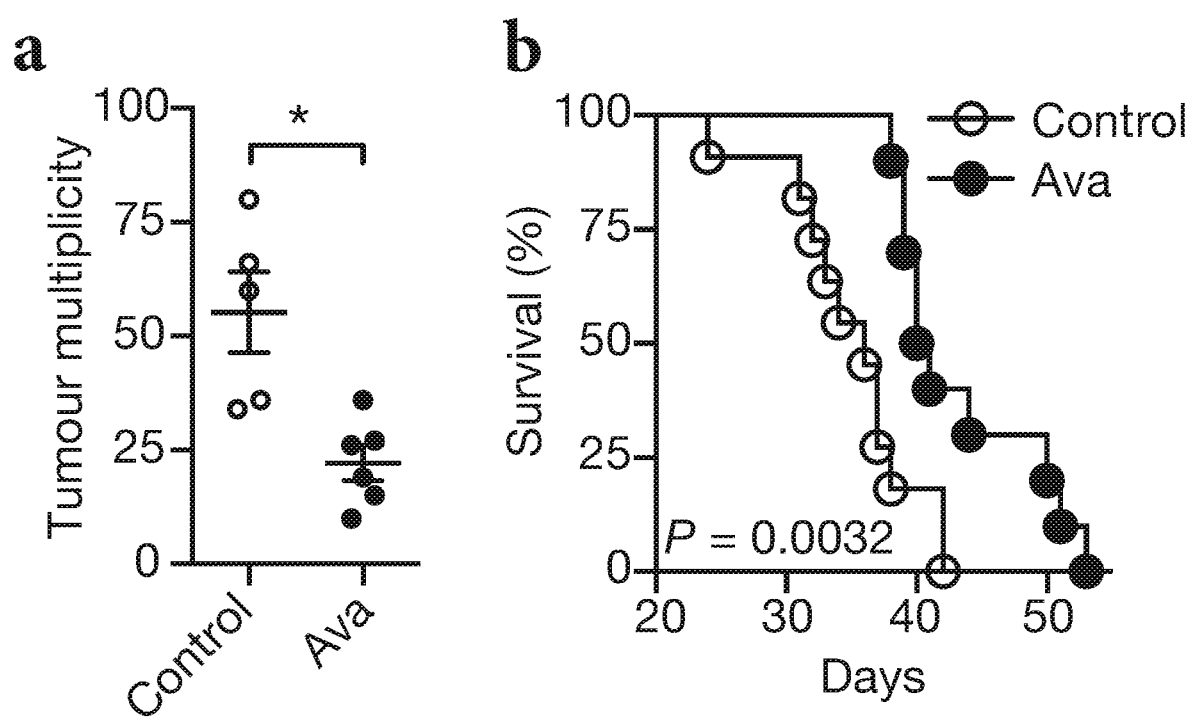
FIG. 10 shows antitumor effect of avasimibe in Lewis lung carcinoma (LLC)
Figure 11:
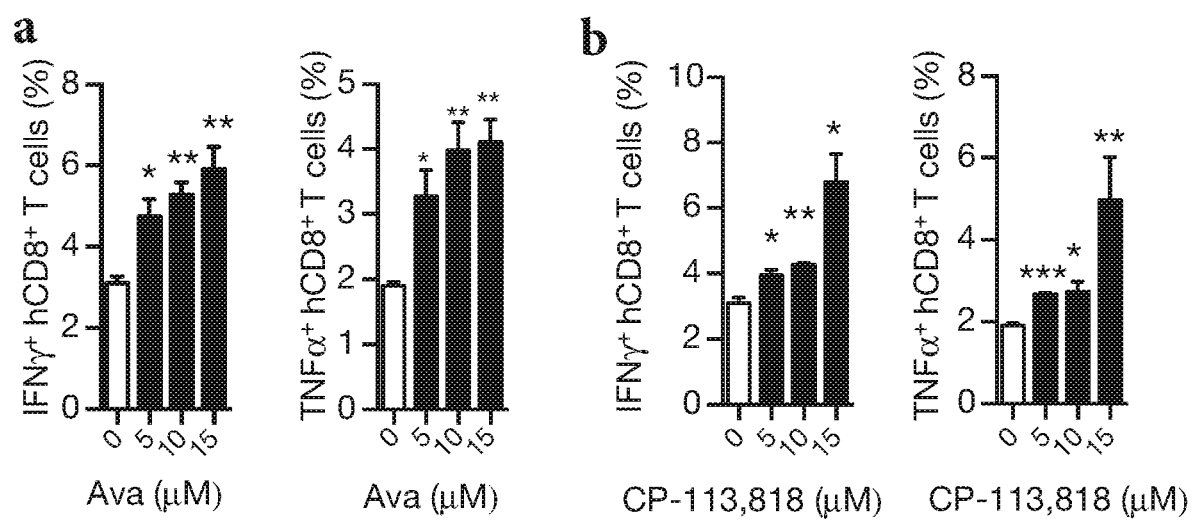
FIG. 11 shows enhanced cytokine production of human CD8+ T cells in response to ACAT1 inhibitors.
Figure 12:
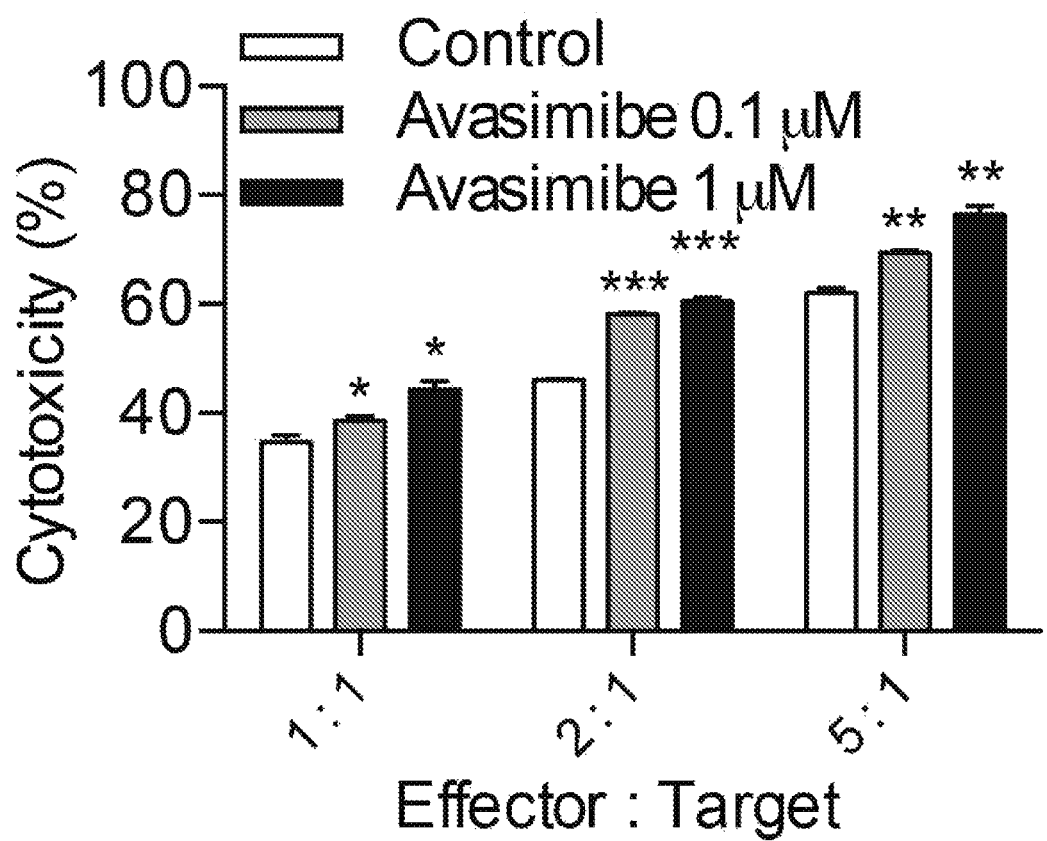
FIG. 12 shows enhanced effector function of mouse CD8+ T cells ex vivo in response to avasimibe.

The phenotypes of avasimibe-treated mice were consistent with those of Acat1$^{CKO}$ mice. Tumour growth was inhibited and survival time was prolonged in the avasimibe-treated mice (FIG. 8). The combined therapy had a better efficacy than monotherapies in inhibiting tumour progression and in increasing survival (FIG. 9). Besides melanoma, avasimibe also showed good antitumor effect in Lewis lung carcinoma (FIG. 10). Moreover, avasimibe enhanced the cytokine production of human CD8$^+$ T cells (FIG. 11). Like other ACAT1 inhibitors, avasimibe can enhance the effector function of mouse CD8$^+$ T cells ex vivo (FIG. 12).

Example 5. Combination of Avasimibe and Dacarbazine

A chemotherapeutic agent, dacarbazine, was used in this study. Melanoma-bearing mice were treated with a combined therapy (avasimibe and dacarbazine) or monotherapies (avasimibe or dacarbazine), and tumour size and survival were studied.

Figure 13:
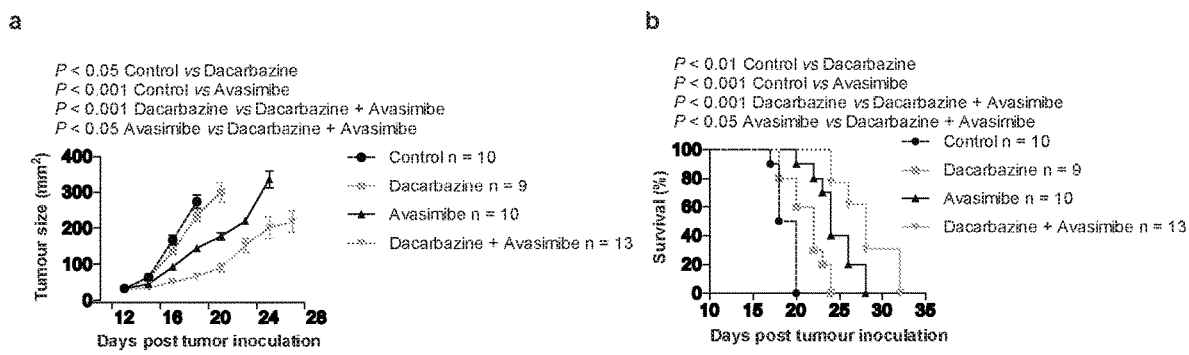
FIG. 13 shows synergistic effect of a combined therapy of avasimibe and dacarbazine in treatment of melanoma.

The combined therapy of avasimibe and dacarbazine had a better efficacy than monotherapies in inhibiting tumour progression and in increasing survival in a melanoma mouse model (FIG. 13, panels a and b).

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for treating a cancer in a patient having a suppressed CD8+ T cell in a tumor microenvironment which has reduced cytotoxic activity, reduced proliferative activity or reduced infiltration activity as compared to a CD8+ T cell not in the tumor microenvironment, comprising administering to the patient a therapeutically effective amount of an acyl-coenzyme A:cholesterol acyltransferases 1 (ACAT1) inhibitor and optionally a second anticancer agent, wherein the ACAT1 inhibitor is selected from the group consisting of a small inhibitory RNA (siRNA), a small hairpin RNA (shRNA), a microRNA (miRNA), an anti-sense nucleic acid, a small molecule inhibitor, and combinations thereof; or is selected from the group consisting of avasimibe (CI-1011), pactimibe, purpactins, manassantin A, diphenylpyridazine, glisoprenin A, CP113,818, K604, beauveriolide I, beauveriolide III, U18666A, TMP-153, YM750, GERI-BP002-A, Sandoz Sah 58-035, VULM 1457, Lovastatin, CI976, CL-283,546, CI-999, E5324, YM17E, FR182980, ATR-101 (PD132301 or PD132301-2), F-1394, HL-004, F-12511 (eflucimibe), cinnamic acid, cinnamic, Dup 128, RP-73163, pyripyropene C, FO-1289, AS-183, SPC-15549, FO-6979, Angekica, ginseng, Decursin, terpendole C, beauvericin, spylidone, pentacecilides, CL-283,546, betulinic acid, shikonin, esculeogenin A, Wu-V-23, pyripyropene A, B, and D, glisoprenin B-D, saucerneol B, sespendole, diethyl pyrocarbonate, beauveriolide analogues, Acaterin, DL-melinamide, PD 138142-15, CL277,082, EAB-309, Enniatin antibiotics, Epi-cochlioquinone A, FCE-27677, FR186485, FR190809, NTE-122, obovatol, panaxadiols, protopanaxadiols, polyacetylenes, SaH 57-118, AS-186, BW-447A, 447C88, T-2591, TEI-6522, TEI-6620, XP 767, XR 920, GERI-BP001, gomisin N, gypsetin, helminthosporol, TS-962, isochromophilones, kudingosides, lateritin, naringenin, and combinations thereof.

2. The method of claim 1, wherein the cancer is selected from the group consisting of melanoma, lymphoma, esophageal cancer, liver cancer, head and neck cancer, bladder cancer, endometrial cancer, kidney cancer, thyroid cancer, breast cancer, colorectal cancer, leukemia, lung cancer, pancreatic cancer, and prostate cancer.

3. The method of claim 1, wherein the cancer is selected from the group consisting of melanoma, lymphoma, esophageal cancer, liver cancer, head and neck cancer, bladder cancer, endometrial cancer, kidney cancer and thyroid cancer.

4. The method of claim 1, wherein the cancer is melanoma selected from the group consisting of Lentigo maligna, Lentigo maligna melanoma, superficial spreading melanoma, acral lentiginous melanoma, mucosal melanoma, nodular melanoma, polyploid melanoma, desmoplastic melanoma, amelanotic melanoma, and soft-tissue melanoma.

5. The method of claim 1, wherein the ACAT1 inhibitor is selected from the group consisting of avasimibe, K604 and CP113,818.

6. The method of claim 3, wherein the ACAT1 inhibitor is selected from the group consisting of avasimibe, K604 and CP113,818.

7. The method of claim 1, wherein the ACAT1 inhibitor is administered intravenously, intramuscularly, parenterally, nasally, or orally.

8. The method of claim 1, wherein the ACAT1 inhibitor is conjugated to a targeting molecule that recognizes CD8+ T cell.

9. The method of claim 8, wherein the targeting molecule is an antibody or fragment thereof.

10. The method of claim 1, wherein the anticancer agent is an alkylating antineoplastic agent.

11. The method of claim 10, wherein the alkylating antineoplastic agent is a triazene.

12. The method of claim 11, wherein the triazene is selected from the group consisting of dacarbazine, mitozolomide and temozolomide.

13. The method of claim 10, wherein the ACAT1 inhibitor is selected from the group consisting of avasimibe, K604, and CP113,818.

14. The method of claim 12, wherein the ACAT1 inhibitor is avasimibe.

15. The method of claim 1, wherein the ACAT1 inhibitor is administered prior to, after, or concurrently with the alkylating antineoplastic agent.

* * * * *